United States Patent [19]

Lees

[11] Patent Number: 5,693,326
[45] Date of Patent: *Dec. 2, 1997

[54] PRODUCING IMMUNOGENIC CONSTRUCTS USING SOLUBLE CARBOHYDRATES ACTIVATED VIA ORGANIC CYANYLATING REAGENTS

[75] Inventor: Andrew Lees, Silver Spring, Md.

[73] Assignee: Henry M. Jackson Foundation for the Advancement of Military Medicine, Rockville, Md.

[ * ] Notice: The portion of the term of this patent subsequent to Mar. 22, 2012, has been disclaimed.

[21] Appl. No.: 456,694

[22] Filed: Jun. 1, 1995

Related U.S. Application Data

[63] Continuation of Ser. No. 408,717, Mar. 22, 1995, which is a continuation-in-part of Ser. No. 124,491, Sep. 22, 1993, abandoned.

[51] Int. Cl.$^6$ .................. A61K 39/385; C07K 17/10
[52] U.S. Cl. .................. 424/194.1; 424/178.1; 424/193.1; 424/197.11; 530/403; 530/411
[58] Field of Search .................. 424/146.1, 196.11, 424/197.11, 178.1, 193.1; 530/406, 411, 403

[56] References Cited

U.S. PATENT DOCUMENTS

| | | |
|---|---|---|
| 3,788,948 | 1/1974 | Kagedal et al. |
| 4,910,135 | 3/1990 | Tischer et al. ............ 435/28 |
| 4,931,392 | 6/1990 | Rehner et al. |
| 5,177,059 | 1/1993 | Handley et al. |

FOREIGN PATENT DOCUMENTS

| | | |
|---|---|---|
| 186576 | 7/1986 | European Pat. Off. |
| 0 428 486 A1 | 5/1991 | European Pat. Off. |
| 1815332 | 7/1969 | Germany |
| WO 93/15760 | 8/1993 | WIPO |

| | | |
|---|---|---|
| WO95/08348 | 3/1995 | WIPO |

OTHER PUBLICATIONS

Carpenter et al., "Preparation of heparin–glyceryl controlled–pore glass affinity media for the separation of α– and β–lipoproteins," Journal of Chromatography, vol. 573, 1992, pp. 132–135.

Andersson et al., "Binding of Epidermal Growth Factor–Dextran Conjugates to Cultured Glioma Cells," Int. J. Cancer, vol. 47, 1991, pp. 439–444.

"CDAP: Monoclonal Coupler," Research Organics Inc. (Cleveland Ohio).

Wakselman et al., "1–Cyano–4–dimethylamino–pyridinium Salts: New Water–soluble Reagents for the Cyanylation of Protein Sulphydryl Groups," J.C.S. Chem. Comm., 1976, pp. 21–22.

Kohn et al., "The Use of Cyanogen Bromide and Other Novel Cyanylating Agents for the Activation of Polysaccharide Resins," Applied Biochemistry and Biotechnology, vol. 9, 1984, pp. 285–305.

Brunswick et al., "Picogram Quantities of Anti–Ig Antibodies Coupled to Dextran Induce B Cell Proliferation," The Journal of Immunology, vol. 140, No. 10, 1988, pp. 3364–3372.

Dick, Jr., et al., "Glycoconjugates of Bacterial Carbohydrate Antigens," Conjugate Vaccines, vol. 10, 1989, pp. 48–114.

(List continued on next page.)

Primary Examiner—Ponnathapura Achutamurthy
Attorney, Agent, or Firm—Finnegan, Henderson, Farabow, Garrett & Dunner, L.L.P.

[57] ABSTRACT

The invention relates to a process for producing an immunogenic construct comprising activating at least one first carbohydrate-containing moiety with CDAP, and covalently joining the activated first moiety to a second moiety. Preferably, the first moiety is a polysaccharide and the second moiety is a protein. Immunogenic constructs are prepared by this process using either direct or indirect conjugation of the first and second moieties.

19 Claims, 11 Drawing Sheets

CARBOHYDRATE CONJUGATION

OTHER PUBLICATIONS

Franci et al., "Letter to the editors Re: Trinitrophenyl-protein conjugates are more complex than it is currently thought," Journal of Immunological Methods, vol. 86, 1986, pp. 155–156.

Lees et al., "Enhanced immunogenicity of protein-dextran conjugates: I. Rapid stimulation of enhanced antibody responses to poorly immunogenic molecules," Vaccine, vol. 12, No. 13, 1994, pp. 1160–1166.

Wilchek et al., "Affinity Chromatography," Methods in Enzymology, vol. 104, 1984, pp. 3–55.

Köhler et al., "Continuous cultures of fused cells secreting antibody of predefined specificity," Nature, vol. 256, 1975, pp. 495–497.

Wileman et al., "Soluble asparaginase-dextran conjugates show increased circulatory persistence and lowered antigen reactivity," J. Pharm. Pharmacol., vol. 38, 1986, pp. 264–271.

Kagedal et al., "Binding of Covalent Proteins to Polysaccharides by Cyanogen Bromide and Organic Cyanates. I. Preparation of Soluble Glycine-, Insulin-and Ampicillin-dextran," Acta Chemica Scandinavica, vol. 25, No. 5, 1971, pp. 1855–1859.

Monsigny et al., "Colorimetric Determination of Neutral Sugars by a Resorcinol Sulfuric Acid Micromethod," Analytical Biochemistry, vol. 175, 1988, pp. 525–530.

Brinkley, "A Brief Survey of Methods for Preparing Preotein Conjugates with Dyes, Haptens, and Cross-Linking Reagents," Bioconjugate Chem., vol. 3, 1992, pp. 2–13.

Chu et al., "Further Studies on the Immunogenicity of Haemophilus influenzae Type b and Pneumococcal Type 6A Polysaccharide-Protein Conjugates," Infection and Immunity, Apr. 1983, pp. 245–256.

Schneerson et al., "Preparation, Characterization, and Immunogenicity of Haemophilus Influenzae Type b Polysaccharide-Protein Conjugates," The Journal of Experimental Medicine, vol. 152, No. 1, 1980, pp. 361–376.

Kohn et al., "Procedures for the Analysis of Cyanogen Bromide-Activated Sepharose or Sephadex by Quantitative Determination of Cyanate Esters and Imidocarbonates," Analytical Biochem., vol. 115, 1981, pp. 375–382.

Marburg et al., "Bimolecular Chemistry of Macromolecules: Synthesis of Bacterial Polysaccharide Conjugates with *Neisseria meningitidis* Membrane Protein," J. Am. Chem. Soc., vol. 108, 1986, pp. 5282–5287.

Kohn et al., "1-Cyano-4-dimethylamino pyridinium tetrafluoroborate as a cyanylating agent for the covalent attachment of ligand to poly-saccharide resins," FEBS Letters, vol. 154, No. 1, 1983, pp. 209–210.

PRODUCING IMMUNOGENIC CONSTRUCTS USING SOLUBLE CARBOHYDRATES ACTIVATED VIA ORGANIC CYANYLATING REAGENTS

This is a continuation of Ser. No. 08/408,717, filed Mar. 22, 1995, which is a continuation-in-part of Ser. No. 08/124,491, filed Sep. 22, 1993, abandoned.

GOVERNMENT INTEREST

The invention may be manufactured, licensed, and used for U.S. governmental purposes without the payment of any royalties to the patent owner thereon.

BACKGROUND OF THE INVENTION

Certain agents such as tetanus toxoid can innately trigger the immune response, and may be administered in vaccines without modification. Other important agents are not immunogenic, however, and must be converted into immunogenic molecules or constructs before they can induce the immune response.

This invention relates generally to advantageous processes for making immunogenic constructs. The invention also relates to the resulting immunogenic constructs and vaccines prepared therefrom, and the use of such immunogenic constructs.

More specifically, the invention relates to methods of activating carbohydrate-containing antigens for use in preparing immunogenic constructs. Immunogenic constructs are very advantageously prepared by activating a carbohydrate-containing moiety with an organic cyanylating agent such as 1-cyano-4-(dimethylamino)-pyridinium tetrafluoroborate (CDAP).

A variety of cyanylating reagents are known per se, e.g., as reagents for activating insoluble particles to prepare gels for affinity chromatography. See Wilcheck et al., *Affinity Chromatography. Meth. Enzymol.*, 104C:3–55. Wakelsman et al., *J.C.S. Chem. Comm.*, 1976:21 (1976), reported that CDAP is a mild reagent that can be used for modifying protein cysteine groups. Kohn et al., *Anal. Biochem*, 115:375 (1981), compared CDAP, N-cyanotriethyl-ammonium tetrafluoroborate (CTEA), and p-nitrophenylcyanate (pNPC) as activating agents for agarose, an insoluble polysaccharide resin. Other researchers have used CDAP to activate other types of insoluble particles, such as Sepharose and glyceryl-controlled pore glass. See, e.g., Carpenter et al., *Journal of Chromatography*, 573:132–135 (1992).

U.S. Pat. No. 3,788,948 to Kagedal et al. generally describes a method that uses organic cyanate compounds to bind organic compounds containing a primary or secondary amino group to polymers containing one or more hydroxyl and/or primary and/or secondary amino groups, e.g., to bind water-soluble enzymes to water-insoluble polymers. Kagedal et al. describe a method using certain organic cyanate compounds such as pNPC having advantages over cyanogen bromide.

Similarly, Andersson et al., *International Journal of Cancer*, 47:439–444 (1991), report using CDAP to activate a soluble polysaccharide prior to conjugation with protein. They directly conjugated epidermal growth factor (EGF) to low molecular weight 40 kDa dextran activated with cyanate, and used very high dextran to EGF ratios of approximately 50:1 (wt./wt.) to produce dextran-EGF conjugates and studied the binding of this conjugate to cultured cells.

Kagedal et al. and Andersson et al., however, are not concerned with immunogenic constructs. Indeed, conjugates of proteins to low molecular weight dextrans have been reported to be poorly or non-immunogenic. T. E. Wileman, *J. Pharm. Pharmacology*, 38:264 (1985).

The degree of immunogenicity, of course, is an important property of immunogenic constructs for vaccination purposes. The process of vaccination employs the body's innate ability to protect itself against invading agents by immunizing the body with antigens that will not cause the disease but will stimulate the formation of antibodies, cells, and other factors that will protect against the disease. For example, dead organisms are injected to protect against bacterial diseases such as typhoid fever and whooping cough, toxoids are injected to protect against tetanus and diphtheria, and attenuated organisms are injected to protect against viral diseases such as poliomyelitis and measles.

It is not always possible, however, to stimulate antibody formation merely by injecting the foreign agent. The vaccine preparation must be immunogenic, that is, it must be able to induce an immune response. The immune response is a complex series of reactions that can generally be described as follows: (i) the antigen enters the body and encounters antigen-presenting cells that process the antigen and retain fragments of the antigen on their surfaces; (ii) the antigen fragments retained on the antigen-presenting cells are recognized by T cells that provide help to B cells; and (iii) the B cells are stimulated to proliferate and divide into antibody-forming cells that secrete antibodies against the antigen.

Antibodies to most bacterial polysaccharides have been shown to provide protection against infection with encapsulated bacteria. The inability of newborns and infants to mount vigorous responses to T-cell independent (TI) antigens, as exemplified by polysaccharides, has resulted in their extreme susceptibility to life-threatening infections with these organisms. This impaired immune response to TI antigens can be overcome by conjugating T-cell epitopes onto the polysaccharides, thereby converting them into T-cell dependent (TD) antigens.

There are two conjugation methods generally used for producing immunogenic polysaccharide constructs: (1) direct conjugation of carbohydrate and protein; and (2) indirect conjugation of carbohydrates and protein via a bifunctional linker or spacer reagent. Generally, both direct and indirect conjugation require chemical activation of the carbohydrate moiety prior to its derivatization.

Chemical activation refers to the conversion of a functional group to a form that can undergo additional chemical reactions, e.g., the addition of a functional group or of a large moiety such as a protein. Derivatization is the addition of functional chemical group(s) or spacer reagent(s) to a protein.

Unfortunately, artisans have encountered a number of problems in forming immunogenic constructs via conjugation using activation methods. For example, the production of conjugate vaccines has been a formidable challenge, in part, because of the difficulty in activating the polysaccharide and conjugating the protein under conditions that do not lead to their degradation or to the destruction of their immunogenic epitopes. In preparing immunogenic constructs, the method used should be sufficiently gentle to retain important antigenic sites, i.e., epitopes, on the molecules. Thus, it is desirable to maintain the integrity of the structure and to preserve epitopes in these compounds. Unfortunately, the preparation steps currently used in the art are frequently not gentle and can destroy native carbohydrate and/or protein structures.

Moreover, many of the known techniques for carbohydrate modification require anhydrous conditions. Unfortunately, however, carbohydrates are frequently insoluble in organic solvents. Marburg et al., *J. Amer. Chem. Soc.*, 108:5282 (1986).

Thus, although there is a large body of chemical literature describing the modification of carbohydrates, much of it is unsuitable for use with aqueous-based antigens. One approach has been the modification of polysaccharides to enhance their solubility in organic solvents. For example, by replacing the acidic hydrogen on certain acidic polysaccharides with the hydrophobic tetrabutyl ammonium counterion, Marburg et al. were able to solubilize polysaccharides in organic solvents and activate hydroxyls with carbonyl diimidazole, a reagent which must be used in dry solvent. This method is used with polysaccharides, such as *Haemophilus influenzae* PRP and Pneumococcal polysaccharides type 6B and 19F. Coupling of proteins can also be achieved through reductive amination, either using the aldehyde found on the reducing end of the polysaccharide or created by oxidation of the carbohydrate. Both of these approaches have intrinsic limitations and, thus, for high molecular weight polysaccharides, coupling through the reducing end is usually slow and inefficient and oxidation often results in cleavage of the polysaccharide chain or otherwise affects the antigen.

Certain carbohydrates contain groups, such as amino or carboxyl groups, that can be more easily activated or derivatized before conjugation. For instance, the amino groups in Pseudomonas Fisher Type I can be easily derivatized with iodoacetyl groups and bound to a thiolated protein. The carboxyl groups in carbohydrates such as Pneumonococcal type III can be easily activated with water-soluble carbodiimides, such as EDC, and can then be coupled directly to protein. Unfortunately, however, this group of carbohydrates is limited.

Other carbohydrates have aldehyde groups at the terminal reducing end that can be exploited for derivatization and conjugation. It is also possible to create aldehyde groups with oxidizing reagents, e.g., sodium periodate. Aldehyde groups can be condensed with amino groups on protein or with a bifunctional linker reagent. This condensation reaction, especially with the terminal reducing end of a high molecular weight polysaccharide however, often proceeds quite slowly and inefficiently. This is exacerbated when directly conjugating carbohydrate aldehydes to proteins. Thus, yields are often very low using this method. Moreover, sodium periodate may break up carbohydrates into smaller fragments and/or disrupt epitopes, which may be undesirable.

Most carbohydrates must be activated before conjugation, and cyanogen bromide is frequently the activating agent of choice. See, e.g., Chu et al., *Inf. & Imm.*, 40:245 (1983), and Dick & Beurret, "Glycoconjugates of Bacterial Carbohydrate Antigens," *Conjugate Vaccines*, J. M. Cruse & R. E. Lewis (eds.), vol. 10, 48–114 (1989). The first licensed conjugate vaccine was prepared with CNBr to activate HIB PRP, which was then derivatized with adipic dihydrazide and coupled to tetanus toxoid using a water-soluble carbodiimide.

To briefly summarize the CNBr-activation method, cyanogen bromide is reacted with the carbohydrate at a high pH, typically a pH of 10 to 12. At this high pH, cyanate esters are formed with the hydroxyl groups of the carbohydrate. These, in turn, are reacted with a bifunctional reagent, commonly a diamine or a dihydrazide. These derivatized carbohydrates may then be conjugated via the bifunctional group. In certain limited cases, the cyanate esters may also be directly reacted to protein.

The high pH is necessary to ionize the hydroxyl group because the reaction requires the nucleophilic attack of the hydroxyl ion on the cyanate ion ($CN^-$). As a result, cyanogen bromide produces many side reactions, some of which add neo-antigens to the polysaccharides. M. Wilcheck et al., *Affinity Chromatography. Meth. Enzymol.*, 104C:3–55. More importantly, many carbohydrates or moieties such as HIB PRP and Pn6 can be hydrolyzed or damaged by the high pH necessary to perform the cyanogen bromide activation.

Another problem with the CNBr-activation method is that the cyanate ester formed is unstable at high pH and rapidly hydrolyzes, reducing the yield of derivatized carbohydrate and, hence, the overall yield of carbohydrate conjugated to protein. Many other nonproductive side reactions, such as those producing carbamates and linear imidocarbonates, are promoted by the high pH. Kohn et al., *Anal. Biochem*, 115:375 (1981). Moreover, cyanogen bromide itself is highly unstable and spontaneously hydrolyzes at high pH, further reducing the overall yield.

Furthermore, the cyanogen bromide activation is difficult to perform and unreliable. Cyanogen bromide is highly toxic and potentially explosive. Extreme care must be used when working with large quantities as used in manufacture. All operations must be carried out in a suitable fumehood. It is also known to those in the art that the activation is not easily reproducible because some batches of cyanogen bromide work well and some do not. Cyanogen bromide is also poorly soluble in water, making it difficult to control the amount of soluble cyanogen bromide available to react with the carbohydrate. Even use of the same batch of cyanogen bromide and apparently identical reaction conditions do not always lead to identical results.

In addition to these disadvantages, it is very difficult to control the degree of carbohydrate activation achieved by using cyanogen bromide. It is also very difficult to achieve a high level of carbohydrate activation using this method. Increasing the amount of cyanogen bromide present is ineffective and only leads to increased side reactions without an increase in activation. Kohn et al., *Applied Biochem and Biotech*, 9:285 (1984).

Thus, while cyanogen bromide activation has proven to be a very useful reagent, it has a number of limitations. For example, cyanogen bromide requires a high pH (10–12) in order to make the hydroxyls sufficiently nucleophilic to react with the cyanate ion. However, neither CNBr nor the cyanate ester intermediate is stable at high pH, and consequently most of the reagent either hydrolyzes or undergoes nonproductive or unwanted side reactions. Thus, the efficiency of polysaccharide activation is low. Furthermore, the high pH required for activation can hydrolyze or damage many pH-sensitive polysaccharides. In addition, CNBr is toxic and difficult to work with in small quantities.

Moreover, as noted above, other conjugation methods suffer from various drawbacks. For example, although polysaccharides such as *Cryptococcus neoformans* and Pneumococcal polysaccharide type 3 and VI antigen have carboxyl groups that can be activated with carbodiimides in preparation for coupling to a protein, and polysaccharides such as Pseudomonas Fisher type III have amino groups that can be conveniently used, these antigens form a relatively limited group of all polysaccharides. Other approaches are therefore needed to activate or functionalize the majority of polysaccharides.

Thus, there is a need in the art for a method to produce immunogenic constructs that is gentle, maintains the integrity of the structure of the carbohydrates and proteins, preserves epitopes in the compounds, is easy to perform, is reliable, is readily reproducible, is readily scaled up, and works with a wide variety of polysaccharides.

SUMMARY OF THE INVENTION

An object of the invention is to achieve a gentle method for producing immunogenic constructs. Another object is to arrive at a method for making immunogenic constructs that maintains the integrity of the structure of the carbohydrates and proteins, and preserves epitopes in the compounds. An additional object is to achieve a method of manufacturing immunogenic constructs that is easy to perform, reliable, and readily reproducible. A further object is to develop a method for making immunogenic constructs that may be used with a variety of polysaccharides. An additional object is to obtain a convenient method for making soluble conjugate vaccines. Another object is to attain a method that is easily scaled up. These and other objects and advantages of the invention will be apparent from the detailed description below.

The present invention attains the above objects, thereby overcoming the problems and disadvantages of known methods for producing immunogenic constructs, by a conjugation process that employs a carbohydrate activation method that is safe, easy, inexpensive, and gentle to carbohydrates. Moreover, the method advantageously employs a homogeneous reaction.

The method of the present invention advantageously uses an organic cyanylating reagent, most preferably 1-cyano-4-(dimethylamino)-pyridinium tetrafluoroborate (CDAP), to activate carbohydrate-containing moieties. Using the inventive method, a conjugate of a polysaccharide and protein can be prepared where only the polysaccharide is modified, making it possible to recover the protein. Moreover, a conjugate of water-soluble and/or surfactant-soluble moieties may be readily prepared according to the invention.

In one preferred embodiment, the invention comprises directly conjugating the activated carbohydrate-containing moiety to a second moiety, such as a water-soluble protein. In another preferred embodiment, the method of the invention comprises covalently binding a functional (bifunctional or heterofunctional) reagent to the activated carbohydrate-containing moiety, and further reacting the functional reagent with the second moiety, e.g., a T-dependent antigen, to form a conjugate immunogenic construct, wherein the carbohydrate-containing and TD moieties are linked by the spacer or linker formed by the functional reagent.

In another preferred embodiment, the immunogenic construct is a dual-carrier construct of a type described in related U.S. patent application Ser. No. 07/834,067, filed Feb. 11, 1992 (now abandoned), and its continuation-in-part, Ser. No. 08/055,163, filed Feb. 10, 1993 (now abandoned), the specifications of which are incorporated by reference herein. Exemplary primary carriers for such a construct include Pneumococcal type 14 (Pn14) and DNA polymers.

The invention is advantageously applicable to a wide variety of soluble carbohydrate-containing moieties, which after activation with CDAP may be either directly conjugated to protein or indirectly conjugated to protein through a spacer or a linker. The invention enables others to produce more effective immunogenic constructs more efficiently and less expensively than immunogenic constructs prepared using known methods.

Moreover, because CDAP and reaction conditions are so gentle, the risk of destruction of carbohydrate structure and, hence, destruction of naturally-occurring epitopes, is greatly diminished. Furthermore, the method has the advantages summarized in Table 1 below in comparison with the presently used method employing cyanogen bromide.

TABLE 1

Comparison of Carbohydrate Activation in the Synthesis of Conjugates

| CNBr | CDAP |
|---|---|
| High pH (10–12) | Near neutral or mildly basic pH (e.g., 7–9) |
| Destroys many CHO epitopes | Little of no alteration of CHO epitopes |
| High toxicity (fume-hood required) | Low toxicity |
| Dangerous in large quantities | Safe in large quantities |
| Difficult to work with small quantities | Easy to work with small quantities |
| Low yields | High yields |
| Multiple side reactions | Minimal or no side reactions |
| Does not easily permit direct conjugation to protein | Allows direct conjugation to protein and enables recovery of unconjugated protein |
| Batch-to-batch variation | Reproducible |

Additional advantages to using CDAP are that it can be prepared in advance and stored in a solution for several months, and the concentration of active reagent can be easily determined from its absorbance at 301 nm (Kohn et al., Anal. Biochem, 115:375 (1981)). This makes it possible to standardize the reagent concentration and makes the carbohydrate derivatization more reproducible, which is important for its use in vaccine preparation.

The above-mentioned advantages apply both to the direct conjugation of proteins to carbohydrates and to indirect conjugation via a spacer. Additional objects and advantages of the invention will be apparent from the detailed description and the drawings.

DETAILED DESCRIPTION AND PREFERRED EMBODIMENTS

Figure 1:
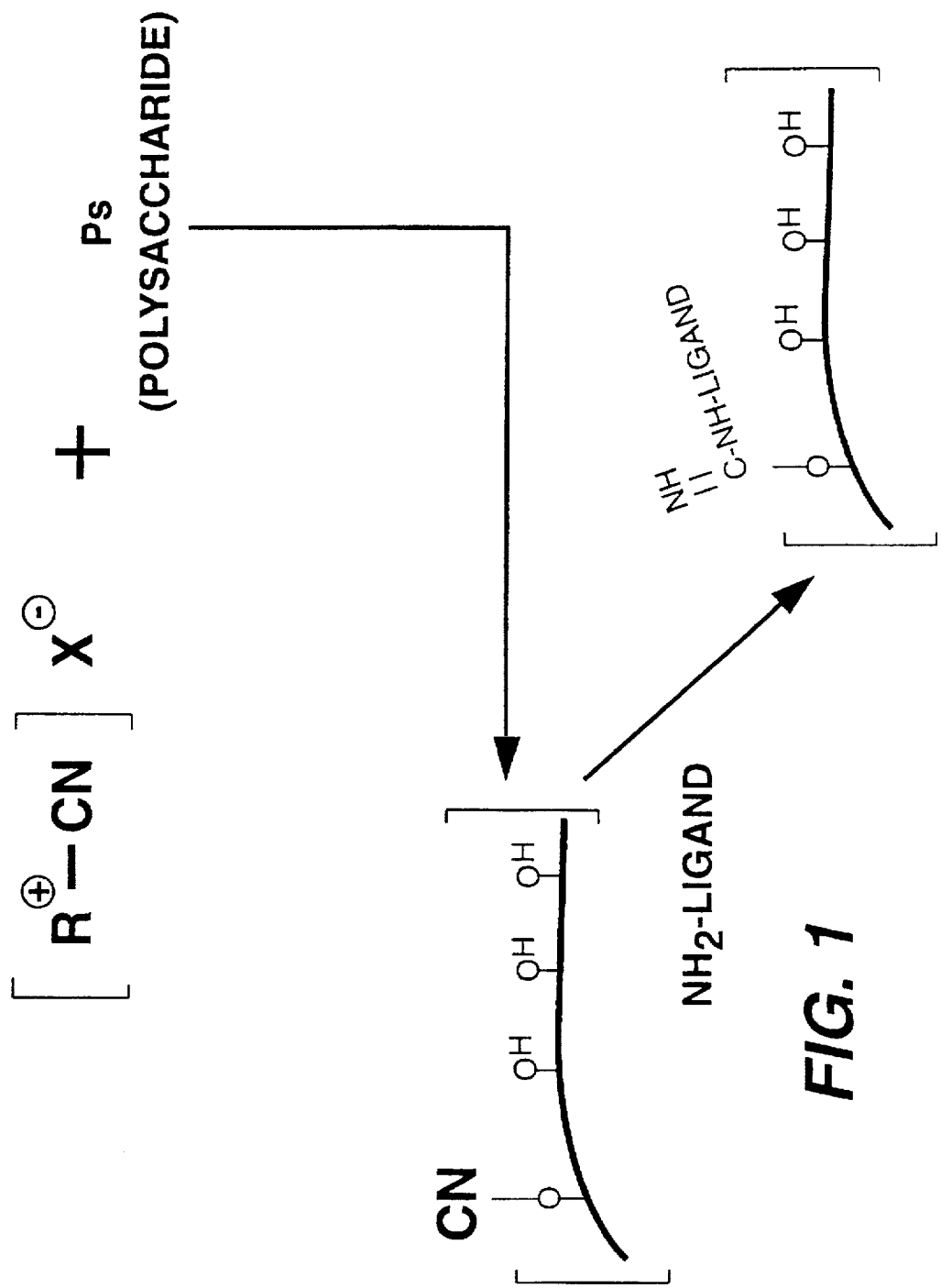
FIG. 1 depicts an example of a generalized scheme for the activation of carbohydrate using organic cyanylating reagents.
Figure 2:
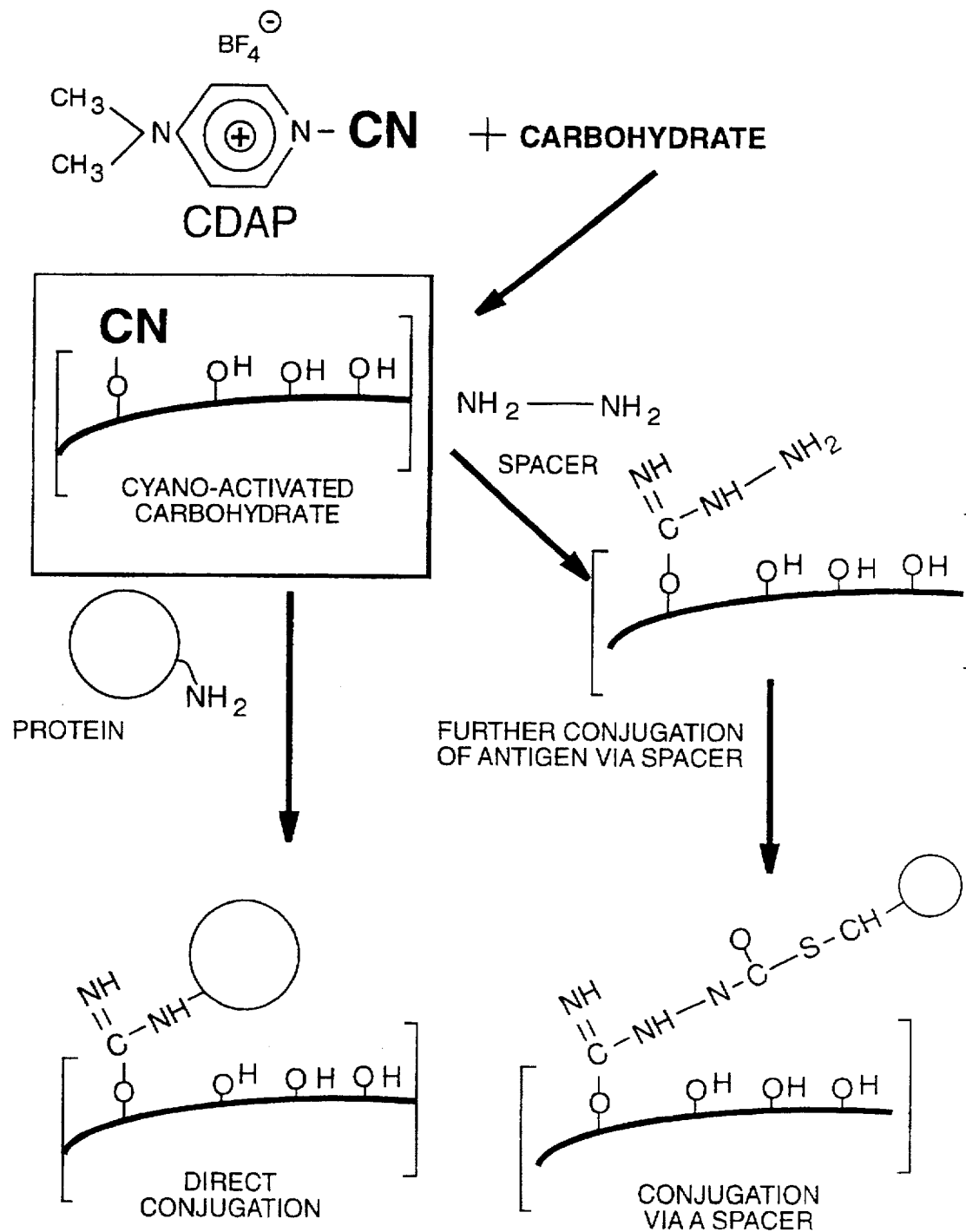
FIG. 2 depicts an exemplary scheme for conjugation of an activated carbohydrate to protein, with direct conjugation shown at the bottom left-hand side and indirect conjugation using a bifunctional reagent shown at the bottom right-hand side.

A generalized scheme for the activation of carbohydrates using organic cyanylating reagents (which may be represented generally by the formula R—CN or {R$^+$—CN}X$^-$, where R is an organic moiety and X is a counter-ion) is shown in FIG. 1. FIG. 2 illustrates the conjugation of an activated carbohydrate to protein.

As used herein, "immunogenic construct" refers to an entity that can stimulate the immune response. The immunogenic construct comprises at least one first moiety conjugated to at least one second moiety. As used herein, a "moiety" is any substance that can be used to stimulate the immune system either by itself or upon being coupled.

Exemplary moieties include carbohydrates, synthetic polymers such as polyvinyl alcohol, proteins and glycoproteins, peptides, other antigens, adjuvant molecules, haptens, DNA, and combinations and derivatives thereof. Haptens refer to small molecules, such as chemicals, dust, and allergens, that by themselves are not able to elicit an antibody response, but can once they are coupled to a carrier, e.g., TNP. An antigen is any molecule that, under the right circumstances, can induce the formation of antibodies. These haptens and antigens may derive from but are not limited to bacteria, rickettsiae, fungi, viruses, parasites, drugs, or chemicals. They may include, for example, small molecules such as peptides, oligosaccharides (e.g., the polyribosyl-ribitol-phosphate oligomers of H. influenzae), DNA oligomers, lipids, toxoids, endotoxin, etc. Preferred moieties are soluble in water or solubilized in surfactant.

In a preferred embodiment, the first moiety is a carbohydrate-containing moiety. As used herein, "carbohydrate" means any soluble monosaccharide, disaccharide, oligosaccharide, or polysaccharide. Preferably, the first moiety is a polysaccharide, more preferably a water-soluble polysaccharide. Preferred polysaccharides include those listed in the chart below of exemplary vaccines.

The carbohydrate-containing moiety is preferably naturally occurring, a semisynthetic, or a totally synthetic large molecular weight molecule. In a preferred embodiment, at least one carbohydrate-containing moiety is selected from E. coli polysaccharides, S. aureus polysaccharides, dextran, carboxymethyl cellulose, agarose, Pneumococcal polysaccharides (Pn), Ficoll, Cryptococcus neoformans, Haemophilus influenzae PRP, P. aeroginosa, S. pneumoniae, lipopolysaccharides, Group A and B streptococcus, N. meningitidis, and combinations thereof.

In an especially preferred embodiment, the carbohydrate-containing moiety is a dextran. As used herein, "dextran" (dex) refers to a polysaccharide composed of a single sugar, which may be obtained from any number of sources (e.g., Pharmacia). Another preferred carbohydrate-containing moiety is Ficoll, which is an inert, semisynthetic, non-ionized, high molecular weight polymer.

The carbohydrate-containing moiety is activated using an organic cyanylating reagent. Preferred organic cyanylating reagents are 1-cyano-4-(dimethylamino)-pyridinium tetrafluoroborate (CDAP), N-cyanotriethylammonium tetrafluoroborate (CTEA), and p-nitrophenylcyanate (pNPC). Of these reagents, CDAP is the most preferred. Other organic complexes with the cyanate group, optionally with a variety of counter-ions, may be used. Particularly preferred organic cyanylating reagents are those with non-nucleophilic counter-ions such as tetrafluoroborate.

After activation via the organic cyanylating reagent, the first moiety is conjugated to the second moiety. Preferably, the second moiety is a protein, which may be selected from viral, bacterial, parasitic, animal, and fungal proteins. Especially preferred second moieties include lipoproteins, bovine serum albumin (BSA), tetanus toxoid (TT), pertussis toxoid (PT), diphtheria toxoid (DT), heat shock protein, T-cell superantigens, and bacterial outer-membrane protein, all of which may be obtained from biochemical or pharmaceutical supply companies or prepared by standard methodologies (see, e.g., J. M. Cruse & R. E. Lewis, (eds.), Conjugate Vaccines in Contributions to Microbiology and Immunology, vol. 10 (1989), which is incorporated herein by reference). Other suitable proteins may be selected from those known in the art.

Figure 3:
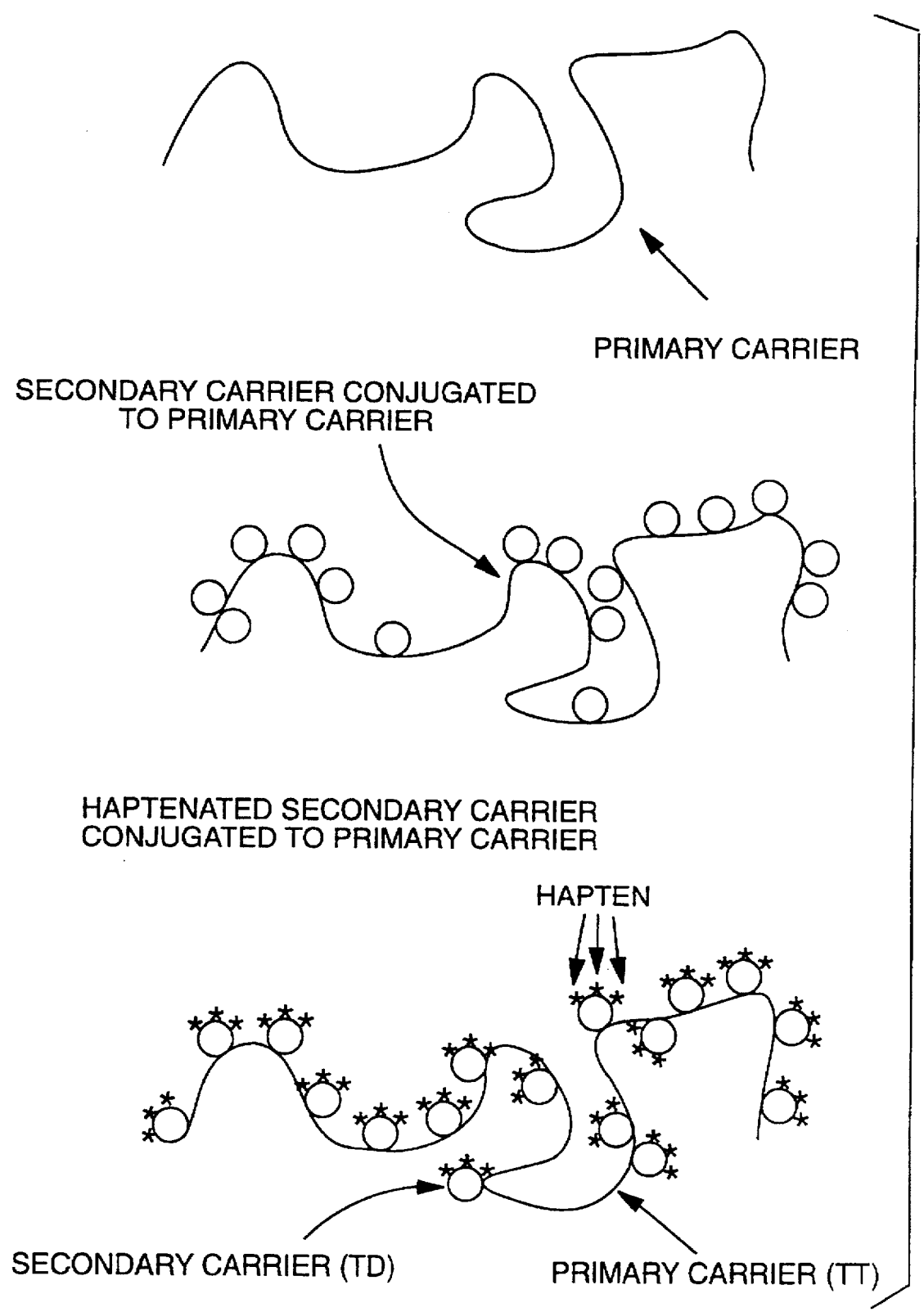
FIG. 3 shows a model of an immunogenic construct.

Other preferred embodiments of the second moiety are albumin, a toxoid, a peptide, a T-cell or B-cell adjuvant, or any other compound capable of activating and recruiting T-cell help. The second moiety may be a T-dependent antigen as represented in FIG. 3.

The second moieties of the invention are capable of being conjugated to at least one carbohydrate-containing moiety. The second moieties may either contain functional groups that can react with the carbohydrate-containing moiety or can be chemically manipulated to be capable of reacting with the carbohydrate-containing moiety.

Numerous copies of specific second moieties as well as a variety of second moieties may be conjugated to the carbohydrate-containing moiety. Coupling of multiple copies of the second moiety to the first moiety significantly augments antibody production to the second moiety.

The inventive process allows one to advantageously control the physical and chemical properties of the immunogenic construct. In accordance with the invention, the artisan may advantageously: modify the charge on the first and second moieties (an advantage in light of evidence that cationized proteins may be more immunogenic); control the size of the construct by varying the size of the carbohydrate-containing moiety; select the degree of crosslinking of the inter- and intra-chain construct (to obtain variations of size and of the three-dimensional matrix); control the number of copies of the second moiety conjugated to carbohydrate-containing moieties; and target to selected cell populations (such as to macrophages to enhance antigen presentation). Dick & Beurret, "Glycoconjugates of Bacterial Carbohydrate Antigens," Conjugate Vaccines, J. M. Cruse a R. E. Lewis (eds.), vol. 10, 48–114 (1989).

The immune response to the construct of the invention may be further enhanced by the addition of immunomodulators and/or cell-targeting moieties. These entities include, for example, (1) detoxified lipopolysaccharides or derivatives, (2) muramyl dipeptides, (3) carbohydrates, lipids, and peptides that may interact with cell surface determinants to target the construct to immunologically relevant cells, (4) interleukins, (5) antibodies, and (6) DNA oligomers.

Thus, in alternative embodiments, third moieties may be conjugated to one or more of the first and/or second moieties using methods such as CDAP activation as described herein or other known techniques. U.S. patent application Ser. Nos. 07/834,067 and 08/055,163 (both applications now abandoned) describe conjugation that promotes enhanced antibody responses to the third moiety. Certain techniques to conjugate various moieties to either the first or second moieties are well known to those skilled in the art, e.g., involving coupling through available functional groups (such as amino, carboxyl, thio and aldehyde groups). See S. S. Wong, *Chemistry of Protein Conjugate and Crosslinking CRC Press* (1991), and Brenkeley et al., "Brief Survey of Methods for Preparing Protein Conjugates With Dyes, Haptens and Cross-Linking Agents," *Bioconjugate Chemistry*, 3:1 (January 1992), which are incorporated herein by reference. Thus, monofunctional reagents may be used as third moieties, e.g., to modify the charge, change the hydrophobicity, label the construct, etc.

In the method of the invention, the carbohydrate-containing moiety is activated using an organic cyanylating reagent. The organic cyanylating reagent is preferably CDAP, which increases the electrophilicity of the cyanate and, when reacted with carbohydrate-containing moieties, transfers a cyano group to the hydroxyl groups of the carbohydrate, thus preparing it for further reaction, i.e., direct or indirect conjugation to protein. The activation reaction can be carried out at neutral pH or under mildly basic conditions (e.g., a pH of about 8 to about 10), which improves the stability and integrity of the polysaccharide and the active intermediate.

CDAP is advantageous because it is highly stable and is relatively safe. CDAP is a water-soluble organic cyanylating reagent in which the electrophilicity of the cyano group is increased, advantageously permitting the cyanylation reaction to be performed under mild conditions. Furthermore, CDAP can be used to activate a wide variety of polysaccharides, which can then be functionalized with diamines or dihydrazides. The high levels of activation and mild conditions of the CDAP cyanylation reaction permit proteins to be directly conjugated to polysaccharides in a one-pot reaction, thereby simplifying the preparation of conjugate vaccines that induce antibody responses to both the polysaccharide and the protein components, even in the absence of a spacer molecule. The ease of use of CDAP facilitates the preparation of protein-polysaccharide conjugate vaccines under a variety of conditions, thus making possible the study of the important parameters of the immunogenicity of conjugate vaccines. Moreover, CDAP-activated polysaccharides can be used to prepare a variety of other useful immunological reagents, e.g., biotinylated polysaccharides and antibody-linked dextrans such as $H\delta^a/1$.

The activation is preferably performed at a pH of from about 6 to about 10, more preferably of from about 9 to about 10. The pH may be adjusted by a variety of techniques (e.g., using a buffer, adding NaOH, etc.) to suit the particular construct being prepared. For example, the activation may be carried out in a variety of solvents using one or more of a variety of suitable non-nucleophilic buffers known in the art. Suitable solvents include saline, water, and some organic solvents. Examples of suitable non-nucleophilic buffers include triethyl amine (TEA), 4-(2-hydroxyethyl)-1-piperazine-ethane sulfonic acid (HEPES), phosphate, carbonate, and borate. Preferably, triethyl amine (TEA) is used as a buffer.

In a preferred embodiment of the invention, CDAP is dissolved in a stock solution at a concentration of 100 mg/ml in dry acetonitrile or up to 75 mg/ml in water. Depending on the nature of the carbohydrate-containing moiety used and the degree of activation desired, various amounts of CDAP may be optimal.

In a preferred embodiment, the concentration of the carbohydrate-containing moiety is from 1 to 20 mg/ml, more preferably from 1 to 15 mg/ml. The activation reaction can be performed successfully with concentrations of carbohydrate-containing moiety up to about 100 mg/ml.

Preferably, the CDAP to carbohydrate-containing moiety ratio for direct conjugation of protein is from about 100:1 to about 500:1 moles CDAP per 100 kDa of the carbohydrate-containing moiety. In another preferred embodiment, the CDAP to carbohydrate-containing moiety ratio for indirect conjugation of protein using a spacer is from 10:1 to 500:1 moles CDAP per 100 kDa of carbohydrate-containing moiety. Depending on the nature of the moieties and the conditions used, different moiety ratios may be optimal.

Unreacted CDAP and reaction by-product such as dimethylaminopyridine can be removed before derivatization or coupling to protein using a suitable purification technique, preferably under acidic conditions, such as dialysis, ultrafiltration, or absorption to suitable bioprocessing beads such as SM4 beads (BioRad). Purified activated polysaccharide can also be prepared by precipitation, e.g., with cold ethanol.

In a preferred embodiment, a carbohydrate-containing moiety that has been activated using CDAP is directly conjugated to the second moiety to produce an immunogenic construct. In another preferred embodiment of the invention, the carbohydrate-containing moiety which has been activated is covalently linked to a suitable bifunctional or heterofunctional reagent. Examples of such functional reagents include ethylene diamine, 1,6-hexane diamine, adipic dihydrazide, cystamine, lysine, glutamic acid, thiol hydrazides, and thiol amines, suitably protected as necessary. See Wong et al., "Chemistry of Protein Conjugate and Crosslinking," *CRC Press* (1991). The second moiety is then covalently linked to the functional reagent, which has already been covalently linked at its other terminus to the carbohydrate-containing moiety.

A preferred pH range for the coupling reaction is from about 7 to about 9, more preferably about 7 to about 8.5. For conjugating a polysaccharide such as dextran, the pH is preferably from about 7.4 to about 8.

A polysaccharide is conjugated to a protein at a ratio in the range of from about 1:1 to about 3:1, e.g., 1:1, using CDAP in one preferred embodiment. For optimal results, high polysaccharide concentrations are avoided. Preferred constructs include tetanus conjugated to a Pneumococcal polysaccharide and tetanus conjugated to *Haemophilus influenzae* PRP. Other preferred conjugates prepared according to the invention include TT-PRP, Pn14-TT, Pn23-TT, malaria-derived peptide-Pn14, DT-Pn14, Pn6-TT, Pn19-TT, and peptide-TT-Pn.

In a preferred embodiment, triethylamine (TEA) is used to facilitate the cyanylation reaction, which may proceed via the formation of an intermediate Von Braun complex. TEA can be replaced by other tertiary amines capable of forming a Von Braun complex. J. Von Braun, *Chem. Ber.*, 33:1438 (1900).

For certain conjugation reactions, glycine, amino ethanol, or other amino-containing reagents may be used to quench the reaction. Such quenching reagents may also be used as one way to modify the net charge of the conjugate.

In another embodiment, the invention relates to vaccines that are made up of an immunogenic construct together with a pharmaceutically acceptable medium or delivery vehicle. Such vaccines will contain an effective therapeutic amount of the immunogenic construct together with a suitable amount of vehicle so as to provide the form for proper administration to the patient. These vaccines may comprise alum or other adjuvants.

Exemplary pharmaceutically acceptable media or vehicles are sterile liquids, such as water and oils, including those of petroleum, animal, vegetable or synthetic origin, such as peanut oil, soybean oil, mineral oil, sesame oil, and the like. Saline is a preferred vehicle when the pharmaceutical composition is administered intravenously. Aqueous dextrose and glycerol solutions can also be employed as liquid vehicles, particularly for injectable solutions. Suitable pharmaceutical vehicles are described in E. W. Martin, *Remington's Pharmaceutical Sciences*, specifically incorporated herein by reference.

The vaccines that may be prepared in accordance with the invention include, but are not limited to, those listed in the chart below:

CHART

Diphtheria vaccine
Pertussis (subunit) vaccine
Tetanus vaccine
H. influenzae type b (polyribose phosphate)
S. pneumoniae, all serotypes
E. coli, endotoxin or J5 antigen (LPS, Lipid A, and Gentabiose
E. coli, O polysaccharides (serotype specific)
Klebsiella, polysaccharides (serotype specific)
S. aureus, types 5 and 8 (serotype specific and common protective antigens)
S. epidermidis, serotype polysaccharide I, II, and III (and common protective antigens)
N. meningitidis, serotype specific or protein antigens
Polio vaccine
Mumps, measles, rubella vaccine
Respiratory syncytial virus
Rabies
Hepatitis A, B, C, and others
Human immunodeficiency virus I and II (GP120, GP41, GP160, p24, others)
Herpes simplex types 1 and 2
CMV (cytomegalovirus)
EBV (Epstein-Barr virus)
Varicella/Zoster
Malaria
Tuberculosis
*Candida albicans*, other candida
Pneumocystis carinii
Mycoplasma
Influenzae viruses A and B
Adenovirus
Group A streptococcus
Group B streptococcus, serotypes, Ia, Ib, II, and III
*Pseudomonas aeroginosa* (serotype specific)
Rhinovirus
Parainfluenzae, types 1, 2, and 3
Coronaviruses
Salmonella
Shigella
Rotavirus
Enteroviruses
Chlamydia trachomatis and pneumoniae (TWAR)
*Cryptococcus neoformans*

The invention also relates to the treatment of a patient by administration of an immunostimulatory amount of the vaccine. The term "patient" refers to any subject for whom the treatment may be beneficial, and includes mammals, especially humans, horses, cows, dogs, and cats, as well as other animals, such as chickens. An "immunostimulatory amount" refers to that amount of vaccine that is able to stimulate the immune response of the patient for the prevention, amelioration, or treatment of diseases. The vaccine of the invention may be administered by any suitable route, but is preferably administered by intravenous, intramuscular, intranasal, or subcutaneous injection.

The invention also relates to a method of preparing an immunotherapeutic agent against infections caused by bacteria, viruses, parasites, fungi, or chemicals by immunizing a patient with the vaccine described above so that the donor produces antibodies directed against the vaccine. Antibodies may be isolated or B cells may be obtained to later fuse with myeloma cells to make monoclonal antibodies. The making of monoclonal antibodies is generally known in the art (see Kohler et al., *Nature*, 256:495 (1975), specifically incorporated herein by reference). As used herein, "immunotherapeutic agent" refers to a composition of antibodies that are directed against specific immunogens for use in passive treatment of patients. A plasma donor is any subject that is injected with a vaccine for the production of antibodies against the immunogens contained in the vaccine.

EXAMPLE 1

Derivatization of a Carbohydrate-Containing Moiety with a Spacer

Materials

CDAP, pyridine, hexane diamine, sodium borate, HEPES, and triethylamine (TEA) were purchased from Aldrich (Milwaukee, Wis.). The carbohydrate-containing moiety, T2000 dextran, with an average molecular weight of 2000 kDa, was obtained from Pharmacia (Piscataway, N.J.).

A stock of CDAP in dry acetonitrile at 100 mg/ml was stored at −20° C. and kept on ice when in use. T2000 dextran was made up at 10.5 mg/ml in saline plus 0.02% azide. Aqueous triethylamine stock was made up at 0.2M and kept on ice during use.

Hexane diamine was made up at 0.5M in 0.1M sodium borate.

Amino group determination was made using trinitrobenzene sulfonate (TNBS) and an extinction coefficient of 11,000 $m^{-1}$ at 366 nm. Franci et al., *J. Imm. Methods.*, 86:155 (1986). Carbohydrate was assayed by the method of M. Monsigny et al., *Anal. Chem.*, 175:525 (1988), using T2000 dextran as the standard.

Control Reactions

The following experiments demonstrate the importance of the components used in the derivatization reaction of the invention. The results show that the amino groups in the final conjugate are covalently linked to the carbohydrate and their presence is not due to artifact or "carryover" of reagent into the final product. Reactions were carried out on ice. For trials performed, omission or substitution of reagents was as indicated in Table 2.

In the procedure using all reagents (line 1 of Table 2), CDAP was added to a vortexed solution of 300 µl dextran (3.1 mg) and returned to the ice bucket. Thirty seconds later, the TEA was added to the vortexed solution. Two minutes after the CDAP was added, 200 µl of the diamine was added and the solution kept on ice for another hour. Samples were dialyzed overnight, filtered with a Millex GV filter, and further desalted on a 1×15 cm P6DG column (BioRad).

As shown in Table 2 below, amino groups were optimally incorporated into dextran in the presence of dextran, CDAP, TEA, and hexane diamine. The data in Table 2 further demonstrate that the amino groups detected are not due to carryover of unconjugated reagents into the final products. Although these results show that TEA is not necessary for derivatization, they show less derivatization when TEA is not present (probably due to a low pH, as later discussed).

TABLE 2

| # | Saline | Dextran | 100 mg/l CDAP | 0.2 M TEA | 0.5 M Hexane Diamine | 0.1 M Borate | NH₂/ Dextran* |
|---|--------|---------|---------------|-----------|----------------------|--------------|---------------|
| 1 | 0      | 300 µl  | 15 µl         | 15 µl     | 300 µl               | 0            | 64            |
| 2 | 300 µl | 0       | 15 µl         | 15 µl     | 300 µl               | 0            | 0             |
| 3 | 0      | 300 µl  | 0             | 15 µl     | 300 µl               | —            | 0             |
| 4 | 0      | 300 µl  | 15 µl         | 0         | 300 µl               | —            | 2.1           |
| 5 | 0      | 300 µl  | 15 µl         | 15 µl     | 0                    | 300 µl       | 0             |
| 6 | 300 µl | 0       | 15 µl         | 0         | 0                    | 0            | 0             |

*Moles NH₂ per 100 kDa dextran.

Derivatization of T2000 Dextran with Hexane 1,6-Diamine

This experiment demonstrates that CDAP can be used to derivatize carbohydrates to introduce amino groups at both high and low ratios. Dextran T2000 was used as a model carbohydrate. Dextran is a polymer made up of glucose monomers.

The first step in the preparation of many conjugate vaccines is the addition of a spacer (Dick & Beurret, "Glycoconjugates of Bacterial Carbohydrate Antigens," *Conjugate Vaccines*, J. M. Cruse & R. E. Lewis (eds.), Vol. 10, pp. 48–114 (1989)). This series of experiments, summarized in Table 3, emphasizes the ease with which a spacer can be added to polysaccharides.

for high levels of NH₂ incorporation. Thus, minimal modification of dextran polysaccharide is necessary for high NH₂-group incorporation.

Furthermore, since an undetermined amount of the active cyanate ester is hydrolyzed without adding a spacer, the CDAP/glucose ratio is an overestimate of the degree of modification of the polymer. Thus, the actual degree of modification is less than the calculated CDAP/glucose ratio.

The degree of incorporation of spacer groups at the lowest reagent dose tested (line 1), 3.1%, is comparable to that used for the synthesis of conjugate vaccines (Chu et al., *Inf. & Imm.*, 40:245 (1983); Dick & Beurret, "Glycoconjugates of Bacterial Carbohydrate Antigens," *Conjugate Vaccines*, J. M. Cruse & R. E. Lewis (eds.), Vol. 10, pp. 48–114 (1989).

TABLE 3

| #  | Dextran (µl) | CDAP (µl) | TEA (µl) | Diamine (µl) | 10⁻³ mole CDAP/mole Dextran | NH₂/* Dextran | % Efficiency (NH2/CDAP)** | %*** Derivat'd |
|----|--------------|-----------|----------|--------------|-----------------------------|---------------|---------------------------|----------------|
| 1  | 600          | 5         | 5        | 600          | .68                         | 17            | 50.0                      | 3.1            |
| 2  | 600          | 10        | 10       | 600          | 1.36                        | 33            | 48.5                      | 5.9            |
| 3  | 600          | 15        | 15       | 600          | 2.03                        | 25            | 24.8                      | 4.6            |
| 4  | 300          | 15        | 15       | 200          | 4.06                        | 30            | 16.7                      | 6.1            |
| 5  | 300          | 30        | 30       | 200          | 8.12                        | 48            | 11.8                      | 8.2            |
| 6  | 300          | 60        | 60       | 200          | 16.24                       | 84            | 4.2                       | 6.2            |
| 7  | 300          | 120       | 120      | 200          | 32.48                       | 112           | 6.9                       | 20.4           |
| 8  | 300          | 15        | 15       | 200          | 4.06                        | 38            | 18.7                      | 6.9****        |
| 9  | 300          | 30        | 30       | 200          | 8.12                        | 62            | 15.3                      | 11.3****       |
| 10 | 300          | 60·       | 60       | 200          | 16.2                        | 35            | 4.3                       | 6.4****        |
| 11 | 600          | 15        | 15       | 600          | 2.03                        | 19            | 18.8                      | 3.5            |

*Moles NH₂ per 100 kDa of dextran.
**To calculate this value, NH₂/dextran values were divided by mole CDAP/mole dextran values and multiplied by 100%.
***Percent of glucose unit within dextran bound to an NH₂ group.
****Experiment carried out at room temperature.

The experiment was conducted at two temperatures. In the runs summarized in lines 1–7 and 11 of Table 3, all reagents were ice-cold, and in the runs summarized in lines 8–10, the reagents were at room temperature. Procedures and reagents were used as described above for the experiment summarized in Table 2, and reagent amounts added were as indicated in Table 3. In the run represented by line 11, diamine was added in 0.15M HEPES. The reaction was slightly less efficient at lower pH. In another embodiment, hexane diamine was made up in 0.1M borate, pH 9.

Efficiency is defined as the number of moles of spacer groups incorporated per mole of CDAP used, expressed as a percentage. The last column (% derivatized) is the percent of the glucose monomer units of the dextran which have been modified with a spacer.

Figure 4:
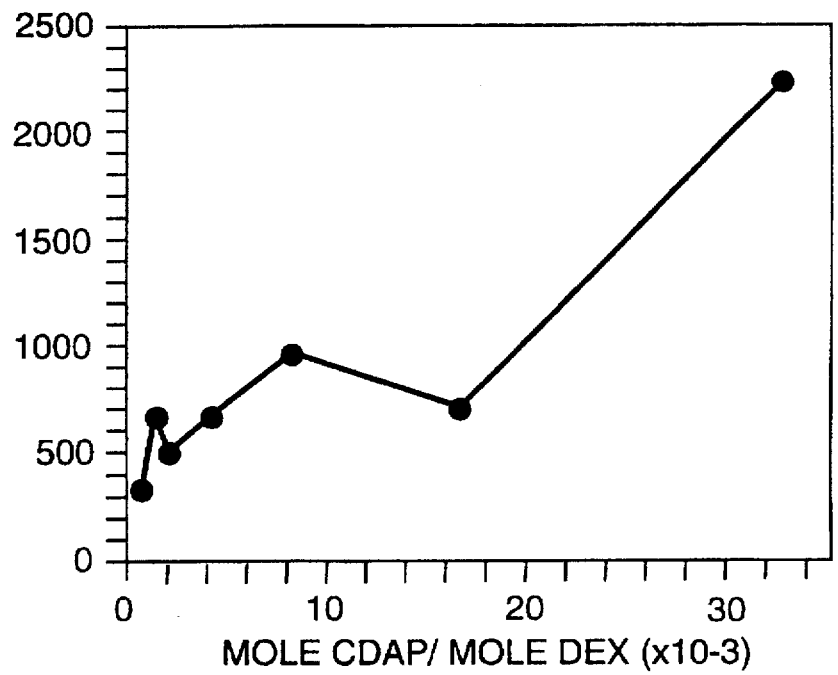
FIG. 4 illustrates the incorporation of $NH_2$ groups into dextran versus the moles of CDAP added per mole of dextran at 10 mg/ml dextran.

The results are further illustrated in FIG. 4, which shows the total number of amino groups (e.g., the spacer reagent added) incorporated versus the moles of CDAP added per moles dextran unit. When this data are converted into NH₂ incorporation versus moles CDAP/mole dextran, it is evident that a CDAP:glucose ratio of less than one is sufficient The table and figure demonstrate the high efficiency of the CDAP reaction for adding spacer reagents. Further optimization of reaction conditions can increase efficiency. Also illustrated is the very high level of incorporation of spacer groups into polysaccharide which is possible using CDAP. At the highest amount of CDAP added (line 7), approximately 1 in 5 of the glucose units was modified (20%) with a spacer. It is not possible to obtain this degree of incorporation of spacer with cyanogen bromide (Kagedal & Akerstrom, *Acta Chemica Scan.*, 25:1855 (1971)).

During the reactions, there was no evident precipitation of the dextran polysaccharide. In contrast, aggregation and precipitation of the polysaccharide can be a problem with the cyanogen bromide method (Kagedal & Akerstrom, *Acta Chemica Scan.*, 25:1855 (1971)).

These reactions were done in small volumes (<1 ml), thus allowing many trial experiments to be conveniently performed. This is important when optimizing a procedure without wasting valuable carbohydrates and proteins. Thus, from the small volumes of reagents exemplified as well as other information set forth herein, the artisan can readily practice the invention using larger amounts as desired in any scale-up for commercial use. In contrast, it is difficult to conveniently work with very small amounts of cyanogen bromide due to its poor water solubility, uncertain potency, and toxicity.

Moreover, comparing lines 8–10 of Table 3 with lines 1–7 and 11, it appears that the level of incorporation of amino groups into dextran was approximately the same when the coupling reaction was carried out at 0° C. or room temperature.

Demonstration of Efficiency of Conjugation Reaction Using CDAP and Verification of Conjugation Using Radiolabeled Protein Since the conjugation reaction using CDAP caused some absorbance at 280 nm, the wavelength normally used to estimate protein concentrations, radiolabeled protein was directly conjugated to dextran. This allowed independent determination of the protein concentration from its specific activity. The yields and recovery of protein were determined.

BSA was lightly radiolabeled with N-hydroxysuccinimide ($^3$H-2,3)-propionate (Amersham), essentially as described by Brunswick et al., *Journal of Immunol.*, 140:3364 (1988). Radiolabeled BSA was dialyzed exhaustively into PBS+ 0.02% azide and subjected to gel filtration chromatography on a S100HR column (Pharmacia) to remove aggregates and concentrated by ultrafiltration using a YM30 filter (Amicon). The BSA concentration was 21 mg/ml, determined from its extinction coefficient at 280 nm (44,000M$^{-1}$). The specific activity of the stock solution, determined by liquid scintillation counting, was 5.48×10$^{12}$ cpm/mole.

Other reagents were as follows: T2000 dextran (approximately 2000 kDa) (Pharmacia) was dissolved at 10.5 mg/ml in water. CDAP was made up at 100 mg/ml in dry acetonitrile, triethanolamine (TEA) was made up at 0.2M in water. Glycine (pH 5.0) was prepared at 1M in water.

Protocol: Reagents were kept on ice and all reactions were performed on ice. The reaction mixture was vortexed during each addition. Twenty-five μl of CDAP was added to 0.5 ml of dextran (5.25 mg), and 30 seconds later 25 μl TEA was added. After a total of 2.5 minutes, 5.25 mg of radioactive BSA was added. Thirty minutes later, the reaction was quenched by the addition of 100 μl of glycine solution and left overnight at 4° C. An aliquot of 0.6 ml was then filtered using a Spin-X membrane (COSTAR). A comparison of the radioactivity aliquots before and after filtration demonstrated that essentially 100% of the radioactivity was recovered in the filtrate. Five hundred μl of the filtrate was applied to a 1×57 cm S400SF gel filtration column (Pharmacia) which was equilibrated with saline plus 0.02% azide, and run at 0.2 ml/min. Fractions of 0.89 ml were collected and analyzed. Dextran concentrations were determined by the method of Monsigny et al. using absorbance at 480 nm. The radioactivity of a 50-μl aliquot taken from each tube was determined by liquid scintillation counting, and $^3$H-BSA concentration was calculated using its specific activity. The position of unconjugated BSA in the column elution was determined in an independent column run.

Figure 5:
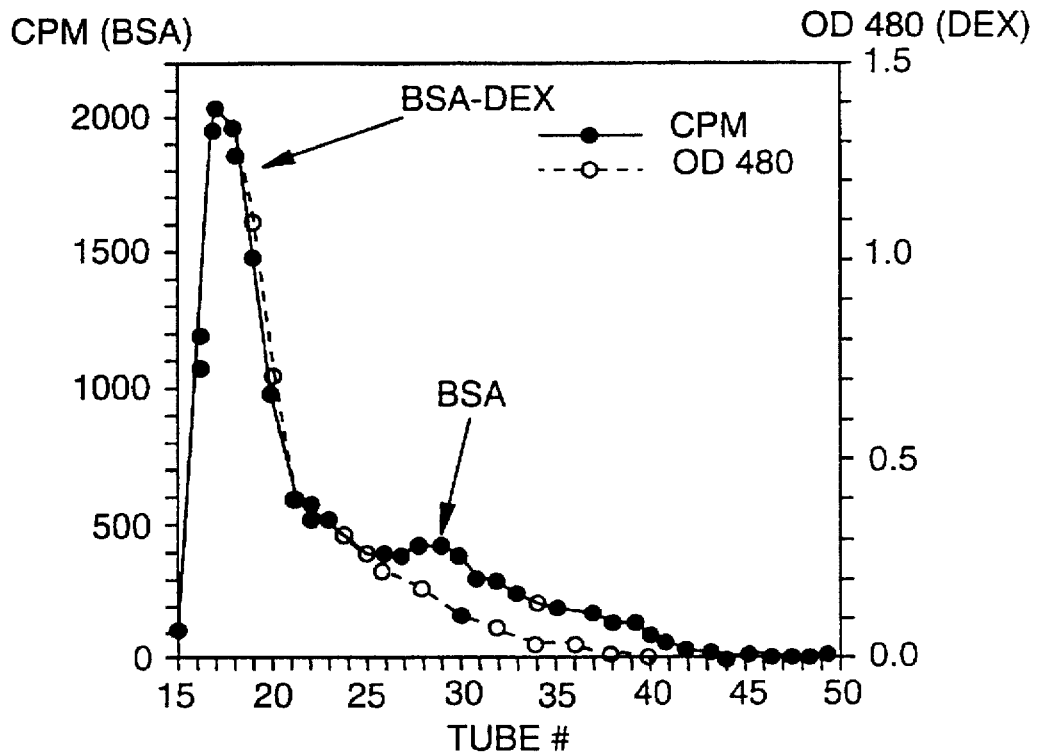
FIG. 5 illustrates the elution profile of a $^3$H-BSA-dextran conjugate from a S400SF gel filtration column.

As shown in FIG. 5, a large portion of the BSA, represented by the cpm, is in a high molecular weight form which runs in an identical position as the dextran, represented by OD480. There is a small residual BSA peak representing unconjugated protein. Table 4 contains the purification data.

TABLE 4

| Total protein recovered: | 3.0 mg |
| Protein applied to column: | 2.9 mg |
| Recovery: | 103% |

TABLE 4-continued

| Protein in high MW form: (tubes 15–23) | >2.0 mg (68%) |
| Ratio of BSA to DEXTRAN for: 2000 kDa dextran | 26 |

The column did not cleanly separate the dextran-BSA conjugate from the unconjugated protein. This is not unusual since the high molecular weight polymers frequently cause tailing in gel filtration columns. Furthermore, since the T2000 dextran was unfractionated, it contained a spectrum of sizes. To estimate the amount of conjugated BSA in the region where free and bound BSA overlap, a constant ratio of bound BSA to dextran was assumed. Total conjugated BSA, calculated by multiplying the BSA:dextran ratio×the total molar amount of dextran, was determined as 2.55 mg. This indicates that 87% of the protein was converted to conjugate form.

TABLE 5

| Mole CDAP/ mole glucose | mole TEA/ mole CDAP | BSA/dextran | % BSA Conjugated |
| --- | --- | --- | --- |
| 0.39 | 1:2 | 26 | 87 |
| 0.39 | 2:1 | 10 | 34 |
| 0.16 | 1:2 | 9 | 28 |
| 0.16 | 5:1 | 1 | 3 |

The results of this BSA-dextran experiment are summarized in Table 5 (line 1) along with three other trials using different amounts of CDAP and TEA (lines 2–4). Both the amount of TEA and the amount of CDAP help get high protein to polysaccharide ratios via direct conjugation. The optimal reagent quantities can easily be determined since the method permits convenient experimentation with small amounts.

It should be emphasized that the direct conjugation reaction does not modify the unconjugated protein, unlike the carbodiimide or heteroligation coupling methods, nor does it use harsh conditions. Thus, one could recover the unconjugated protein for further use. Since many protein antigens are valuable, this is a major advantage of the direct conjugation method.

EXAMPLE 2A

Preparation of PT-Pn14 Conjugates

The purpose of these experiments is to: (1) demonstrate that the transformation of the protein from a low molecular weight form to a high molecular weight form is a result of direct conjugation of the protein to the carbohydrate; (2) determine, under one particular set of conditions, the minimum amount of cyanylating reagent needed to conjugate the protein; and (3) demonstrate that clinically relevant conjugates can be prepared using the method of the invention.

Pertussis toxoid (PT) (from Mass. Public Health Biol. Labs, Boston, Mass.) was dissolved at 0.289 mg/ml in 0.5M NaCl, 0.02M sodium phosphate, pH 8.8. One tenth ml of 0.1M sodium borate, pH 9.1, or 0.75M HEPES, pH 7.5, was added per milliliter of PT. Pneumococcal-type 14 (Pn14) (ATTC lot 83909) was dissolved at 5 mg/ml in 0.15M saline with 0.02% azide. Triethylamine (TEA) was dissolved at 0.2M in water. CDAP was dissolved at 100 mg/ml or 10 mg/ml in acetonitrile (made up and stored at −20° C.). Glycine was made up at 1.0M, pH 5.0. Amino ethanol or other amino reagents can be substituted for glycine/HCl.

Experiment 1

Synthesis of Useful Vaccine Construct with Direct Conjugation: PT-Pn14

Each tube contained 250 µg of Pn14 (50 µl) on ice. At time zero, various amounts of CDAP as indicated in the table were added, and 30 seconds later 25 µl of TEA was added. Two minutes later 1 ml of PT was added. After about 1 hour, 100 µl of glycine solution was added.

Samples were kept at 4° C. overnight. The next day, they were filtered with a Costar 0.45 micron spin filter and run on an HPLC TSK-gel filtration column in 0.2M KCl. Percent HMW is the area of the high molecular weight OD280 conjugate peak versus the OD280 peak indicating unconjugated moiety. It is defined by (percent area void volume peak)/(% area void vol. peak +% area unconjugated moiety peak). The percent areas, obtained from the HPLC runs, were as follows:

TABLE 6

Direct Conjugation Of Pertussis Toxoid to Pn14

| # | µmole CDAP/100 kDa Pn14 | % HMW |
|---|---|---|
| 1 | 1720 | 100.0 |
| 2 | 520 | 52.3 |
| 3 | 172 | 32.8 |
| 4 | 51 | 31.0 |
| 5 | 17 | 28.1 |
| 6 | 0 (PT control) | 22.0 |
| 7 | 0; no TEA, no PT, (Pn14 control) | — |
| 8 | 0; no TEA, no Pn14; PT without Borate | 11.3 |

Because the PT control has a HMW of 22%, there may be a small amount of aggregation of the PT caused by the reaction conditions. This set of data also indicates that by varying the CDAP to polysaccharide (Ps) ratio, it is possible to control the ratio of protein to carbohydrate in the final conjugate.

Experiment 2

Conjugation of a Monosaccharide to PT

In this series, 150 µl of a solution of 10 mg/ml glucose, which is monomeric, was substituted for the Pn14 polysaccharide. Conditions similar to Experiment 1 were used except that the PT was made up in HEPES (pH 7.5, M 0.075) buffer instead of borate. Also, 20 µl instead of 25 µl TEA was used. These conditions yielded the following:

| # | Condition | % HMW form |
|---|---|---|
| 1 | PT only, no CDAP or TEA | >20% |
| 2 | CDAP, TEA (not glucose); + PT | ~0 |
| 3 | Glucose, CDAP, TEA; + PT | ~0 |

Numbers 2 and 3 indicate that CDAP does not polymerize the pertussis toxoid itself and that, therefore, the conversion of the PT to a high molecular weight form is due to its coupling to the high molecular weight polysaccharide and not due to polymerization of the protein. It was evident from the HPLC run that glucose was conjugated to PT because there was a slight increase in the molecular weight of PT.

Experiment 3

Synthesis of Useful Vaccine Construct Via a Spacer: PT-Pn14

Pn14-derivatized with hexane diamine was prepared as follows. Ten µl of CDAP (100 mg/ml in acetonitrile) was added (193 mole CDAP per 100 kDa of polysaccharide). Thirty seconds later 20 µl of TEA (0.2M) was added. After a total of 2.5 minutes had elapsed, 300 µl of 0.5M hexane diamine in 0.1M sodium borate (pH 9.1) was added. After one hour, the solution was dialyzed into water, filtered, and desalted into saline on a P6DG (BioRad) column. The void volume was pooled and concentrated with a Centricon 30 device (Amicon). It was determined to have 33 amino groups per 100 kDa of Pn14 polysaccharide.

Figure 6:
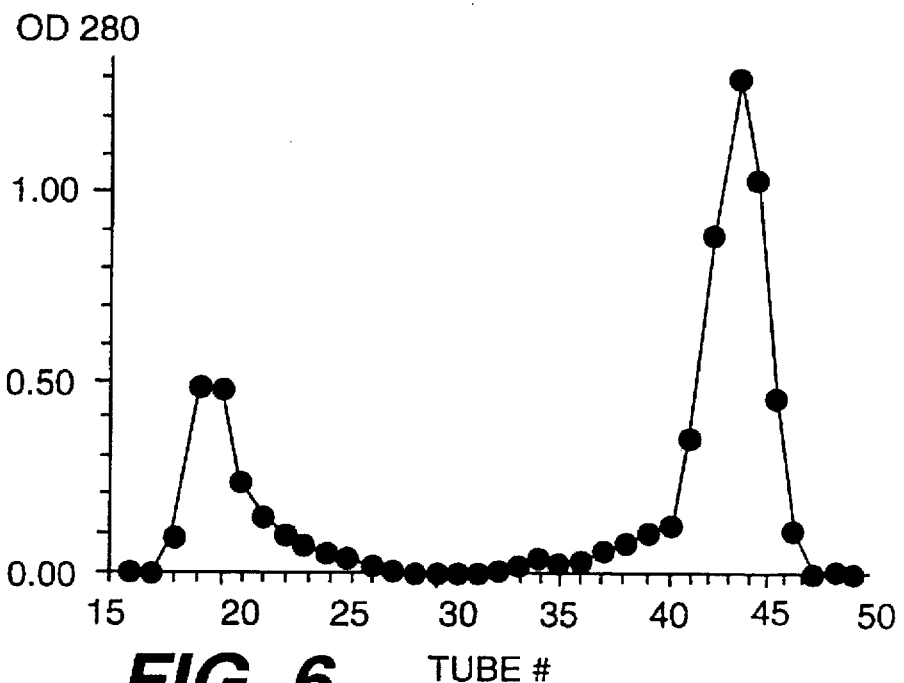
FIG. 6 illustrates the OD280 absorbance of immunogenic constructs prepared according to the method of the invention, eluted from S400SF gel filtration column.

Pertussis toxoid was conjugated to the amino-Pn14 using heteroligation chemistry (Brunswick et al.). Fifty µl of 0.75M HEPES buffer (pH 7.5) was added to 0.44 ml of the amino-Pn14. It was iodoacetylated with 10 µl of 0.1M iodoacetyl propionate N-hydroxy-succinimide (SIAP). Pertussis toxoid was thiolated with a 20-fold molar excess of SATA (Calbiochem, La Jolla, Calif.). Each was desalted into saline, mixed, and 1/9 volume of buffer containing 0.75M HEPES, 10 mM EDTA, and 0.5M hydroxylamine was added. The final volume was 1.1 ml. After an overnight incubation, the solution was made 0.2 mM in mercaptoethanol for one hour and then 10 mM in iodoacetamide for 10 minutes, following which it was fractionated on a S400SF gel filtration column (Pharmacia) (see FIG. 6). The void volume peak was pooled and concentrated by pressure filtration on a PM10 membrane (Amicon). Approximately 50% of the pertussis toxoid was recovered in conjugate form. The final conjugate contained 0.7 moles PT per 100 kDa of Pn14 polysaccharide. Protein concentration in the conjugate was determined by the Bradford assay (BioRad) using PT as the standard. Polysaccharide concentration was determined by the method of Monsigny et al. using Pn14 as the standard.

EXAMPLE 2B

Direct Conjugation of a Protein to Pn14 Using CTEA

CTEA offers the advantage of having fewer side reactions than CDAP and leads to purer products, as described in Kohn et al., *Anal Biochem*, 115:375 (1981). Its disadvantage is that it is moisture sensitive, must be weighed out in a closed vessel, and cannot easily be prepared as a stock solution.

One ml of Pneumococcal type 14 polysaccharide (Pn14) (5 mg/ml in saline) is kept at 0° C. CTEA (Available from Aldrich Chemical, Milwaukee, Wis.) is stored under dry nitrogen. Two mg CTEA is weighed out in a closed weighing vessel and added to the cooled, vigorously mixed Pn14. Twenty µl of TEA (0.2M in water) is immediately added while mixing. Sixty seconds later, 5 mg of pertussis toxoid (1.5 mg/ml) is added to the stirred solution. One-half hour later, the reaction is quenched with 200 µl 1M glycine (pH 5.0). After an additional hour, the solution is filtered and passed over an S400SF gel filtration column, equilibrated with saline. The void volume peak is collected and sterile filtered. A 1:1 conjugate is produced.

Addition of Spacer Reagent to Pneumococcal Type 14 Polysaccharide Using CTEA

One ml of Pn14 (5 mg/ml in saline) is kept at 0° C. CTEA (available from Aldrich Chemical, Milwaukee, Wis.) is stored under dry nitrogen. One mg CTEA is weighed out in a closed weighing vessel and added to the cooled, vigorously mixed Pn14. Immediately 20 µl is added to TEA (0.2M in water) while mixing. Sixty seconds later, 300 µl of 0.5M hexane diamine in 0.1M borate (pH 9) is added while mixing. After one hour, the solution is exhaustively dialyzed into saline and sterile filtered. Since a ratio of 187 mole CTEA per 100 kDa Pn14 is used, a conjugate with approximately 18 amines per 100 kDa of Pn14 is produced.

EXAMPLE 3

Direct Conjugation of Pertussis Toxoid to Haemophilus Influenzae Polysaccharide (PRP)

Figure 7:
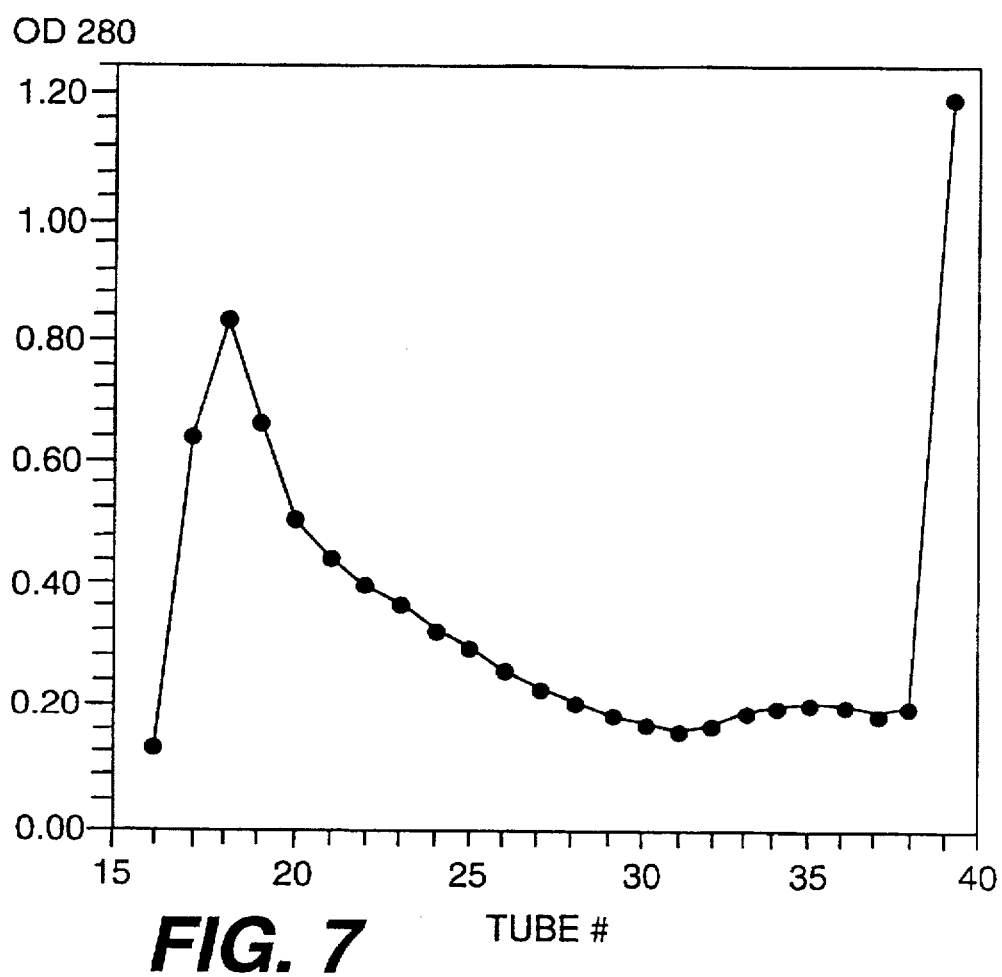
FIG. 7 illustrates the elution profile of $H\delta^a/1$-(CDAP)-dextran from S400SF gel filtration column.
Figure 8:
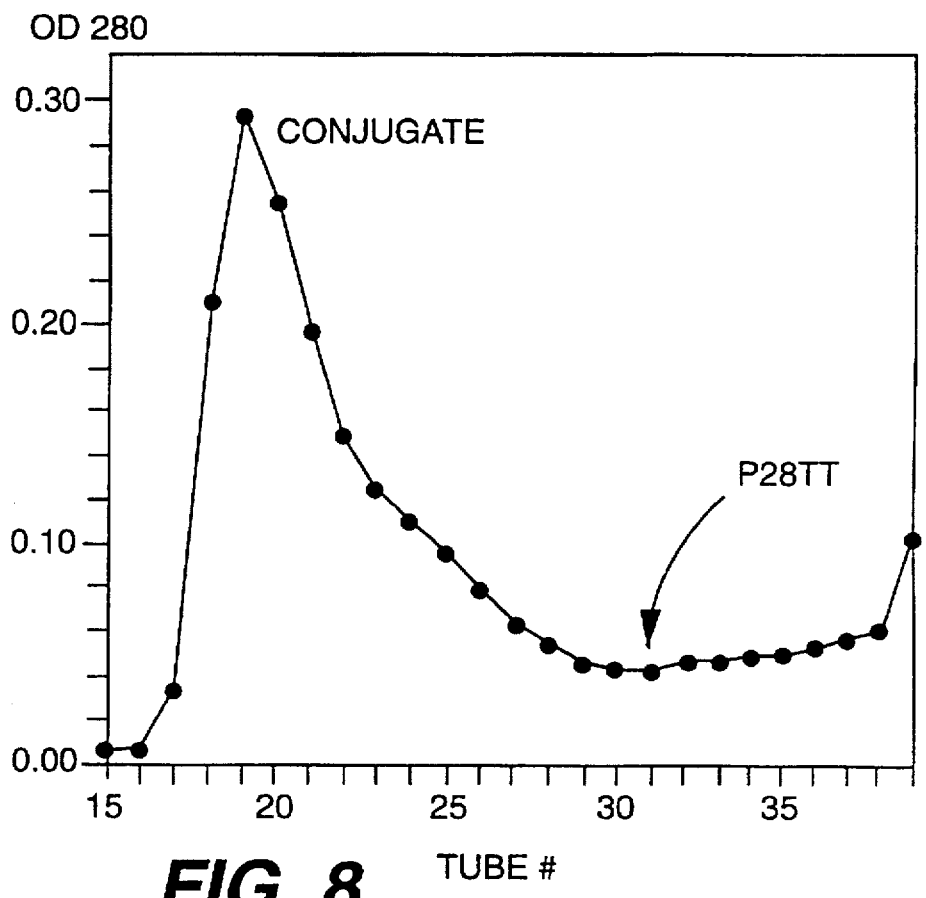
FIG. 8 illustrates OD280 and OD430 values of column samples eluted from S400SF gel filtration column loaded with $H\delta^a/NH_2$-(CDAP)-dextran.

PRP, average MW 350 kDa, was obtained from the Massachusetts Public Health Biological Laboratory. Pertussis toxoid was from the same source. Fifteen μl of CDAP (100 mg/ml) was added to 100 μl (2 mg) of PRP on ice. Thirty seconds later, 30 μl of TEA was added. This represented 319 moles of CDAP per 100 kDa of PRP. After an additional two minutes, 0.75 ml of pertussis toxoid (1.1 mg) was added. Forty minutes later, 200 μl of 1M glycine (pH 5.0) was added to quench the reaction. After one additional hour, the solution was passed over an S400SF gel filtration column equilibrated with saline (see FIG. 7). The void volume was pooled and sterile filtered. The product was determined to have 1.1 PT per 100 kDa of PRP with an overall yield of 68%.

The vaccine prepared by Chu et al., *Inf. & Imm.*, 40:245 (1983), used 377 moles cyanogen bromide per 100 kDa of PRP and had ratios of 1.4 to 2.1 PT per 100 kDa of PRP with yields of less than 50%. Thus, the direct conjugation method of the invention yielded a similar conjugate but with less work, higher yields, and without the use of a toxic reagent.

Since many published protocols for preparing PRP conjugates start with the PRP derivatized with a spacer (Chu et al., Schneerson et al., *J. Exp. Med.*, 152:361 (1980); Dick & Beurret, "Glycoconjugates of Bacterial Carbohydrate Antigens," *Conjugate Vaccines*, J. M. Cruse & R. E. Lewis (eds.), Vol. 10, pp. 48–114 (1989)), CDAP was also used to add a spacer to PRP. The conditions used were as described above but 100 μl of 0.1M hexane diamine in 0.1M borate was added instead of the pertussis toxoid. The product was dialyzed into saline. It was determined to have 102 amino groups per 100 kDa of PRP. Since this is a higher ratio than used in published procedures, even less CDAP could have been used.

EXAMPLE 4

Immunogenic Constructs Useful as Vaccines Prepared Using CDAP Chemistry

Conjugation Using CDAP and a Bifunctional Reagent

In brief, a malaria-derived peptide, p28 (SEQ. ID. NO.:1: Cys Asn Ile Gly Lys Pro Asn Val Gln Asp Asp Gln Asn Lys), from the gamete-specific protein pfs25, was conjugated to tetanus toxoid (TT). P28 has been shown to induce malaria transmission blocking antibodies. CDAP was then used to couple p28-TT to Pneumococcal-type 14 (Pn14) polysaccharide.

FDA-approved tetanus toxoid was dialyzed overnight into HEPES buffer and reacted with a 30-fold molar excess of the iodoacetylating agent (SIAP). After 3 hours, reagents were removed by ultrafiltration using a Macrosep 30 (Filtron Technology) and washed into fresh HEPES, 0.15M, pH 7.5, buffer. Tritium-labeled p28 was added as a solid to the derivatized TT while gently mixing. Following overnight reaction at 4° C., the mixture was treated with 0.2 mM mercaptoethanol to block any remaining active groups and then desalted on a P6DG column equilibrated with HEPES buffer. From the specific activity of the peptide, the product was determined to contain 20 moles p28 peptides/mole of TT. The conjugate was dialyzed into saline and sterile filtered.

Direct Conjugation Using CDAP

Figure 9:
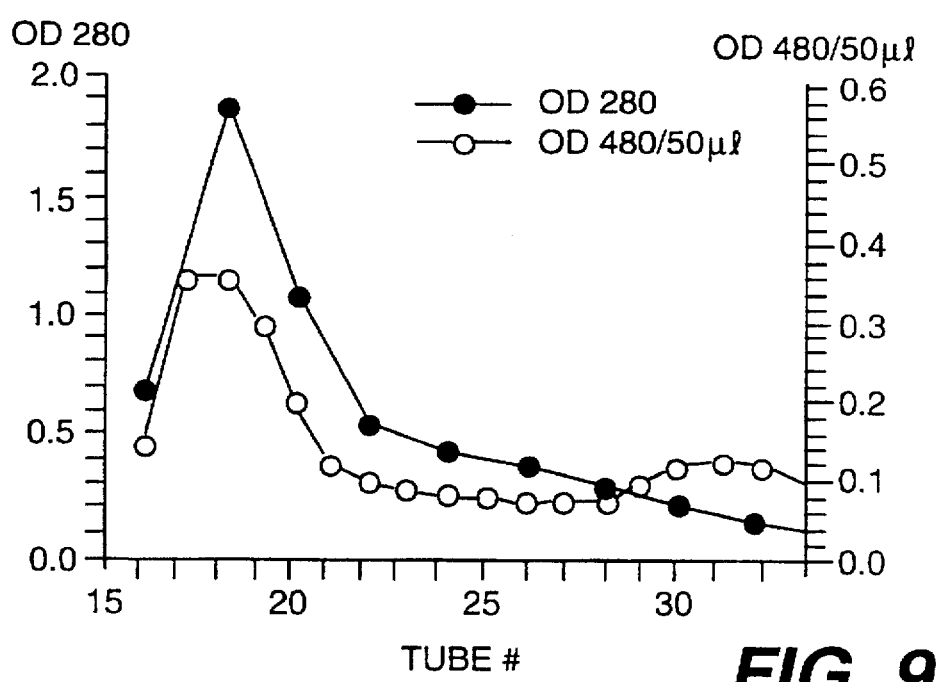
FIG. 9 illustrates the immunoreactivity of immunogenic constructs prepared using the methods of the invention.

Pn14 (obtained from American Tissue Type Collection, ATTC) has a high molecular weight (c.a. $10^6$ daltons). P28-TT was directly conjugated to Pn14 as follows. CDAP (10 μl from a 100 mg/ml stock solution in acetonitrile) was added to Pn14 (1.1 mg in 150 μl saline). Thirty seconds later, 20 μl of triethylamine (0.2M) was added. Two minutes later, 0.55 mg in 0.8 ml saline) of p28-TT was added, and one hour later, the reaction was quenched for another hour with 200 μl 1.0M glycine (pH 5). The conjugate was then passed over an S400SF gel filtration column equilibrated with saline and the void volume containing the conjugate was pooled. FIG. 9 indicates that virtually all of the p28-TT was found in the void volume in conjugated form.

Immunoreactivity of Immunogenic Constructs

Groups of 5 DBA/2 mice were immunized with i.v. with 10 μg p28-TT or (p28-TT)-Pn14 conjugate in saline, bled three weeks later, and the sera assayed by ELISA (enzyme-linked immunoabsorbent assay) for reactivity against recombinant pfs25 protein. Peptide p28 is derived from pfs25. Another set of mice was immunized with the same antigens precipitated with the adjuvant, alum (Imject, Pierce Chemical Co., Rockford, Ill.).

Consistent with the related applications, Table 7 shows that only the high molecular weight conjugate elicited good anti-protein titers.

TABLE 7

| Antigen | Anti-pfs25 IgG1 Titers | |
|---|---|---|
| | i.v. (saline) | s.c. (alum) |
| (p28-TT)-Pn14 | 36 | 346 |
| p28-TT | <10 | <10 |

This demonstrates that the CDAP method can be used to prepare useful vaccine constructs. It also illustrates the ease with which useful conjugates can be prepared.

EXAMPLE 5

Biologically Active Multivalent Protein Constructs Prepared Using CDAP

To demonstrate that conjugates prepared using CDAP to directly couple proteins to polysaccharides could yield a multivalent product (which as set forth in the related applications has enhanced immunogenicity) and that the process could be gentle enough to preserve biological activity, various conjugates of a monoclonal antibody with dextran were prepared. These experiments used monoclonal antibody H$\delta^a$/1 with an anti-IgD antibody which crosslinks membrane IgD on B lymphocytes and induces proliferation (Brunswick et al., *Journal of Immunol.*, 140:3364 (1988)). As described by Brunswick et al., conjugation of multiple copies of H$\delta^a$/1 to a high molecular weight polymer such as 2000 kDa dextran (H$\delta^a$/1-AECM dextran) induced B-cell proliferation at 1000-fold lower concentrations and induced higher levels of proliferation than unconjugated H$\delta^a$/1. In Brunswick et al., a simple, straightforward but multistep, multi-day procedure was required to prepare the conjugate. Aminoethyl carboxymethyl dextran (AECM dextran) was prepared first as described in Brunswick et al. and then heteroligation chemistry was used to couple the H$\delta^a$/1 to the carbohydrate.

H$\delta^a$/1-dextran was prepared by both direct conjugation using CDAP and indirect conjugation using a spacer and CDAP as follows.

Direct conjugation: To a vortexed solution of 3.2 mg of T2000 dextran (Pharmacia) in 0.3 ml saline, 15 μl of CDAP was added (from a 100 mg/ml stock in acetonitrile). Thirty seconds later, 15 μl of 0.2M TEA was added while vortexing. After an additional 2 minutes, 6 mg H$\delta^a$/1 (in 362 μl 10.05M sodium borate and 0.075M NaCl) was added while gently vortexing. After 15 minutes, the reaction mixture was quenched by the addition of 100 μl of 1.0M glycine, pH 5.0, and passed over an S400SF gel filtration column (1×59 cm) equilibrated with saline. The column elution is shown in FIG. 9. The void volume peak was pooled and sterilized with a Millex GV filter. The product is called H$\delta^a$/1-(CDAP)-dextran. This procedure took approximately 3 hours.

Spacer: Dextran was activated with CDAP as above (31.5 mg T2000 dextran in 3 ml saline and 25 µl CDAP followed by 25 µl TEA, 1 mole CDAP/0.06 mole of glucose monomers). Three ml of 0.5M 1,6-diaminohexane in 0.1M sodium borate was added. The solution was exhaustively dialyzed into water and then fractionated on an S400HR gel filtration column. The void volume was pooled and concentrated. This amino-dextran was determined to have 147 amino groups per 2000 kDa dextran. The product is called $NH_2$-(CDAP)-dextran. Including dialysis, this was a two-day procedure. In contrast, AECM-dextran usually takes about one week to prepare using the Brunswick et al. method.

H$\delta^a$/1 was conjugated to AECM-dextran and $NH_2$-(CDAP)-dextran using the heteroligation techniques described in Brunswick et al. The conjugates are called H$\delta^a$/1-AECM-dextran and H$\delta^a$/1-$NH_2$-(CDAP)-dextran, respectively. Conjugation using ACEM-dextran was a two-day procedure.

B-cell proliferation assays, using 10,000 cells/well, were performed as described by Brunswick et al. Table 8 provides the results of those assays, specifically indicating incorporation of tritiated thymidine into B cells as counts per min./well.

TABLE 8

| Mitogen | H$\delta^a$/1 Concentration (µg/ml) | | |
|---|---|---|---|
| | 1 | 0.1 | 0.01 |
| H$\delta^a$/1-AECM-dextran (preparation 1) | 16,045 | 25,774 | 25,850 |
| H$\delta^1$/1-AECM-dextran (preparation 2) | 21,685 | 29,280 | 34,969 |
| H$\delta^a$/1-(CDAP)-dextran | 16,497 | 23,654 | 19,779 |
| H$\delta^a$/1-$NH_2$-(CDAP)-dextran | 19,353 | 28,343 | 25,879 |
| Medium (control) | 760 | 725 | 760 |

As reported in Brunswick et al., H$\delta^a$/1 alone causes no incorporation at these concentrations. Maximum incorporation at 10–100 µg/ml H$\delta^a$/1 is approximately 3000 cpm.

This data indicate that the conjugates prepared using CDAP, with and without a spacer, are essentially equivalent to H$\delta^a$/1-AECM dextran in their abilities to induce proliferation. Since only multivalent antibody induces high levels of proliferation at low doses, all the conjugates must be multivalent. Thus, direct conjugation with CDAP did not affect the biological activity of the antibody. The direct conjugation procedure was markedly faster to prepare than conjugates prepared with a spacer. Further, adding the spacer and conjugating using CDAP was much faster than preparing AECM dextran.

Thus, this experiment illustrates (1) the high yield of a multivalent construct using CDAP and (2) the ease and speed of preparation of conjugates, especially direct conjugates. Conjugation using CDAP and a bifunctional reagent took under 48 hours and direct conjugation took less than three hours.

EXAMPLE 6

Unless indicated otherwise, the protocol in these experiments was generally as follows. Triethylamine (TEA), acetonitrile, sulfuric acid ($H_2SO_4$), resorcinol, hexane diamine, sodium borate, and HEPES were obtained form Aldrich and were of reagent grade or better. N-cyano-4-dimethylaminopyridinium tetrafluoroborate (CDAP) was purchased from Sigma or from Research Organics (Cleveland, Ohio). Trinitrobenzene sulfonic acid (TNBS) was obtained from Kodak Chemicals. Millex filters were obtained from Millipore Corp.

Dextran T2000 was obtained from Pharmacia. Pneumococcal type 14 polysaccharide was obtained from the ATTC (Rockville, Md.). Amino ethyl carbamyl dextran was prepared as described by Brunswick et al. Monomeric BSA (bovine serum albumin) was prepared from low endotoxin Cohen fraction V BSA (Sigma catalogue #A9306) by gel filtration on a 2.6 cm×97 cm S100HR column (Pharmacia), equilibrated with saline plus azide. The product was shown by analytical HPLC to have less than 0.5% dimer and less than 0.1% material of higher molecular weight mass. The BSA was periodically checked by HPLC to confirm its monomeric status. An extinction coefficient of 44,000M$^{-1}$ was used for BSA.

Polysaccharide was activated with CDAP as follows. CDAP was made up at 100 mg/ml in acetonitrile and stored at –20° C. for up to one month. CDAP was slowly pipetted into a vortexed solution of polysaccharide in water, and thirty seconds later, a volume of 0.2M TEA equal to the volume of CDAP used was added. At 2.5 minutes, a one-fifth volume of 0.5M hexane diamine in 0.1M sodium borate (pH 9.3) was added. The reaction proceeded overnight at 4° C. The reaction product was desalted on a P6DG or a P6 cartridge (BioRad), equilibrated with saline, and then further dialyzed into saline. Some samples were concentrated using a Centricon 30 device (Amicon) and desalted again to confirm the removal of free diamine. Variations of this general procedure are indicated below. The extent of derivatization with hexane diamine was determined using a TNBS assay for primary amines. Absorbance was measured at 366 nm, using an extinction coefficient of 11,000M$^{-1}$ (Franci et al.). CDAP-activated dextran, derivatized using ethanolamine instead of diamine, was found to be TNBS negative in this assay. Polysaccharide concentrations were determined as described by Monsigny et al. Results are expressed as moles of amine per 100 kDa of polysaccharide unless indicated otherwise.

Protein conjugation to amino-dextran via a thio-ether linkage was performed as described by Lees et al., Vaccine, 12(3):1160, 1994. Protein was conjugated directly to polysaccharide by activating the polymer with CDAP as described above for derivatization with amines. Protein (10 mg/ml in 0.15M HEPES, pH 7.5) was rapidly added to a gently vortexed solution at 2½ minutes after the CDAP was introduced. Reactions were quenched with approximately ⅕ volume 0.5M ethanolamine in 0.75M HEPES, pH 7.5, for at least one hour before gel filtration on a S300HR or S400HR column (Pharmacia), equilibrated with saline. The peak tube from the void volume was assayed for protein with the Bradford method (BioRad reagent) using BSA as the standard. Polysaccharide concentrations were determined by the method of Monsigny et al., using dextran as the standard. The results, which are discussed below, are expressed as mg of protein per mg of polysaccharide unless indicated otherwise.

Activation of Polysaccharides Using CDAP

Experiments were performed to determine whether CDAP activation of polysaccharides can be used to prepare conjugate vaccines under conditions that are more rapid, more gentle, more convenient, and safer than previously reported methods. As a prototype polysaccharide, high molecular weight dextran (T2000 dextran, Pharmacia) was activated with CDAP under a variety of experimental conditions.

Figure 10:
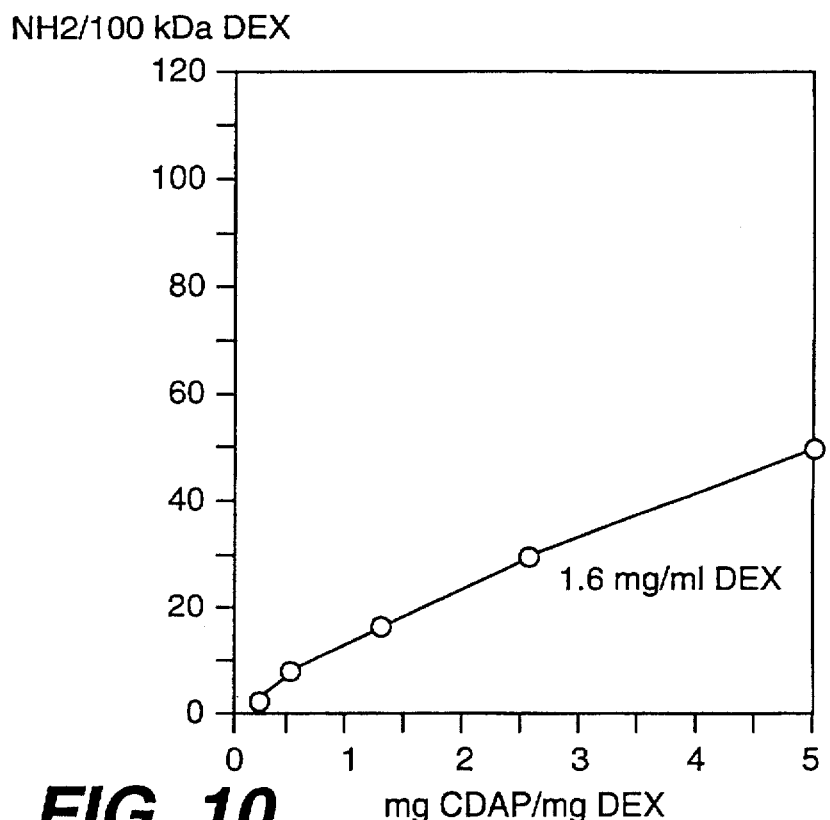
FIG. 10 shows the results of derivatization of dextran (dex) with hexane diamine with CDAP ($NH_2$/100 kDa dex versus mg CDAP/mg dex) at 1.6 mg/ml dextran.

From a 100 mg/ml stock solution, a volume of CDAP was slowly pipetted into a solution of T2000 dextran in water (1.6 mg/ml as shown in FIG. 4, or 10 mg/ml as shown in FIG. 10). At 30 seconds, a volume of 0.2M TEA equal to the volume of CDAP was added, and 120 seconds later, a large excess of hexane diamine in sodium borate (pH 9.3) was quickly added. After desalting on a P6DG column followed by exhaustive dialysis to remove unconjugated reagents, high levels of polysaccharides were found (see FIGS. 4 and 10). Following this same procedure but in the respective absence of CDAP, the dextran, or the diamine, no amines were detectable using the TNBS assay. Furthermore, CDAP-activated dextran reacted with a monoamine (ethanolamine), instead of the hexane diamine, was TNBS negative. To further ensure that all low molecular weight material had been removed, the derivatized polysaccharide was concentrated by ultrafiltration and desalted a second time on a P6DG column. The amine ratio was unchanged after this procedure.

The degree of derivatization was dependent on the amount of CDAP—increases in the CDAP-to-dextran ratio led to increases in the absolute number of amino groups substituted onto the polysaccharide as shown in FIGS. 4 and 10. The extent of derivatization was dependent on the polysaccharide concentration for the same molar CDAP-to-dextran ratio. Thus, at 1.6 mg/ml dextran, efficiencies ranged from 0.7 to 2.4 percent based on moles of amines substituted per mole of CDAP, while at 10 mg/ml dextran, as much as 0.2 mole of amines were substituted per mole of CDAP (20% efficiency).

Figure 11:
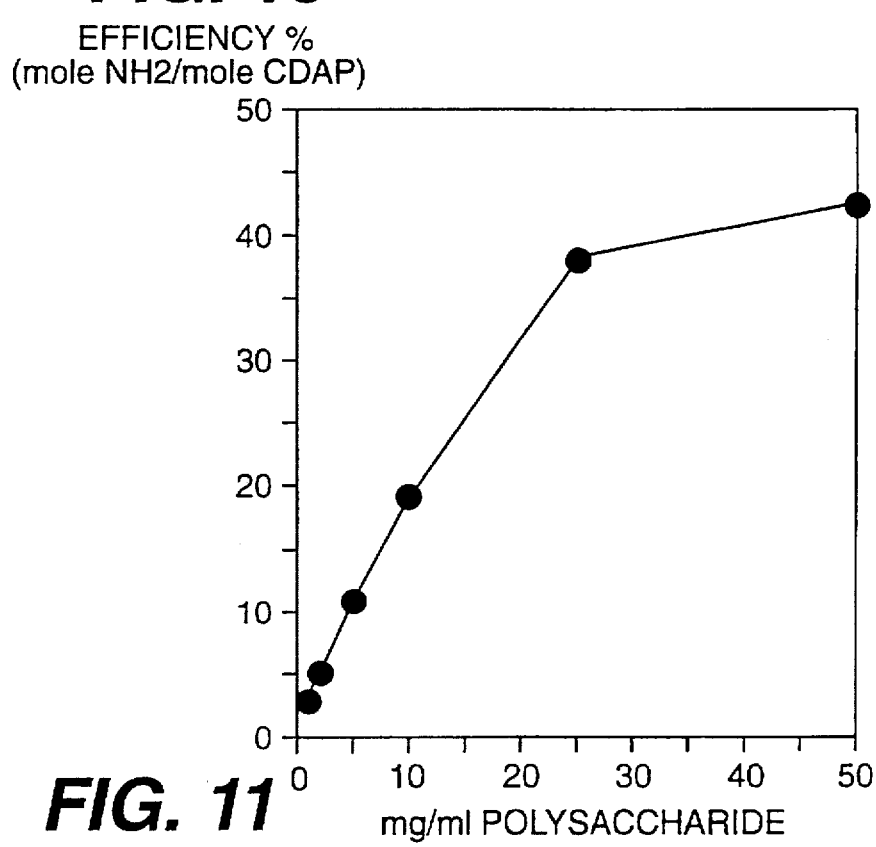
FIG. 11 is a graph of the efficiency of CDAP activation versus the polysaccharide concentration.

In order to improve the efficiency of this bimolecular reaction, the polysaccharide concentration was increased from 1 to 50 mg/ml, using a fixed amount of CDAP (see FIG. 11). At the highest polysaccharide concentration used, more than 0.4 mole of amine was added for every mole of CDAP used. In contrast to the high level of substitution attained with CDAP activation, CNBr activation usually yields maximum efficiencies of about 1 to 2%.

In the absence of TEA, derivatization with diamines was markedly reduced. To determine whether the presence of a tertiary amine such as TEA is essential for activating a soluble polysaccharide with CDAP, the efficiency of activation using TEA was compared with that using inorganic buffer or NaOH.

One hundred µl of a CDAP solution (100 mg/ml in acetonitrile) was slowly added to a stirred solution of 2 ml of T2000 dextran (10 mg/ml in water) at room temperature. After thirty seconds, 1N NaOH was slowly added to maintain the pH at about 9. After 1½ minutes, 1 ml of BSA, 20 mg/ml in 0.5M HEPES, pH 8.0, was added. After the reaction was allowed to proceed for eighteen hours at 4° C., it was quenched by adding 100 µl of 0.5M ethanolamine in 0.75M HEPES, pH 7.5. For analysis, 300 µl of the product was gel-filtered on a 1 cm×50 cm S400HR column equilibrated with saline and azide. The void volume peak tube was assayed for protein using the BioRad assay and for polysaccharide using the resorcinol assay, and was found to have 0.45 mg of BSA per mg of dextran.

As shown in Table 9 below, derivatization resulted with a variety of buffers. Indeed, careful addition of 1N NaOH was used to raise the pH to about nine yielded good levels of substitution.

TABLE 9

Derivatization of dextran with hexane diamine using various buffers (desalted, dialyzed, concentrated, and desalted)

| Buffer | NH$_2$/100 kDa dex |
|---|---|
| TEA (0.2 M) | 29 |
| Borate (pH 8.8) | 40 |
| Carbonate | 20 |
| NaOH | 36 |

With dextran, there were no significant differences in the levels of derivatization over a pH range of from 8 to 10, although other polysaccharides have been found to be more dependent on the activation pH (see below). As noted above, if TEA is omitted and the pH is not raised, the dextran is still activated but it is derivatized to a much lower degree. Thus, CDAP activation or coupling does not depend on the presence of TEA or a buffer—any appropriate means may be used to raise the pH so that the reaction mixture is sufficiently alkaline.

Table 10 shows the reaction kinetics of activation using CDAP. In the experiment, 100 µl CDAP (100 mg/ml acetonitrile) was added to 1 ml dextran (20 mg/ml) at 30 seconds, 1 ml of 0.1M sodium borate, pH 8.8, was added, and after two minutes, 0.5 ml hexane diamine in 0.75M HEPES was added. Aliquots were desalted at the indicated times on a P6 cartridge equilibrated with saline, and then exhaustively dialyzed into saline before analysis. At high concentrations of polysaccharide and CDAP, the solutions gelled. Thus, it is more convenient to work with 10 to 20 mg/ml polysaccharide solutions.

TABLE 10

Kinetics of Reaction of CDAP-Activated Dextran with Hexane Diamine

| Reaction time | NH$_2$/100 kDa dex |
|---|---|
| 15 min. | 42 |
| 1 hr. | 46 |
| 3 hr. | 47 |
| 24 hr. | 48 |

As shown in Table 10, the derivatization reaction was rapid and essentially complete within 15 minutes. No increase in the degree of derivatization was noted at 3 or 24 hours.

To test reproducibility, Pneumococcal polysaccharide type 14 (Pn14) was activated with CDAP and derivatized with hexane diamine. To a stirred solution of 1 ml of Pn14 (10 mg/ml in water) was added 30 µl of CDAP (100 mg/ml in acetonitrile) (0.3 mg CDAP/mg Pn14). After thirty seconds, 30 µl of TEA (0.2M in water) was added. At two minutes, 0.5 ml of hexane diamine (0.5M in 0.75M HEPES, pH 7.6) was added. At 1½ hours, the product was desalted with P6 cartridge, concentrated by ultrafiltration, and again desalted, and then assayed for amines with TNBS and for Pn14 with resorcinol/sulfuric acid. As shown in Table 11, efficiencies of 13–15%, based on moles of amines detected per mole of CDAP used, were obtained in three experiments performed over a one-year period.

TABLE 11

| Experiment | NH$_2$/100 kDa dex | Efficiency (mole NH$_2$/mole CDAP) |
|---|---|---|
| A | 17.9 | 14.1% |
| B | 19.8 | 15.5% |
| C | 17.3 | 13.6% |

The results tabulated above indicate stability of the CDAP reagent in the freezer, reproducibility, and high efficiency. In comparison, CNBr solution is not stable, and the CNBr-activation procedure is difficult to reproduce and has an efficiency of about 2%.

Direct Conjugation of Protein to CDAP-Activated Ps

Figure 12:
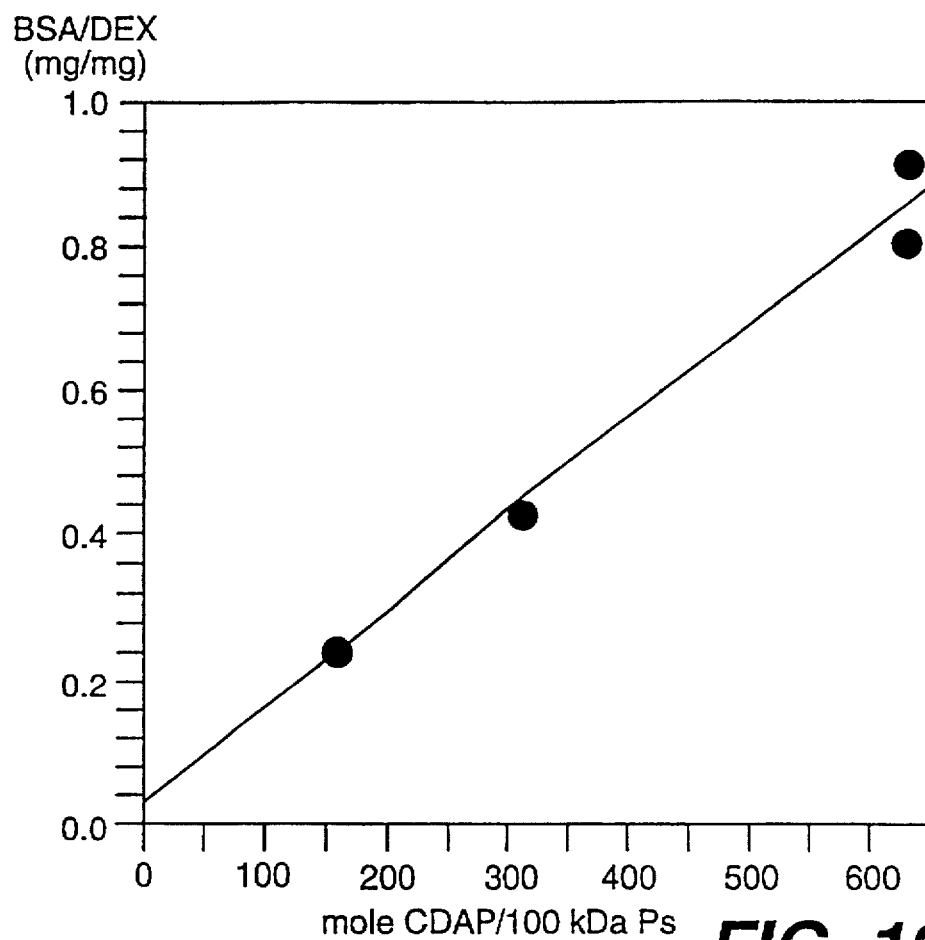
FIG. 12 shows the direct conjugation of BSA to dextran for various CDAP:polysaccharide ratios for CDAP activation.

As with derivatization of amines, the extent of protein conjugation to the polysaccharide was dependent on the amount of CDAP used to activate the polysaccharide. As shown in FIG. 12, at a concentration of 10 mg/ml dextran, the CDAP:dextran ratio linearly increased with the BSA:dextran ratio of the product. Similar ratios of BSA:dextran could also be observed at even lower CDAP:dextran ratios if the protein and/or polysaccharide concentrations were increased.

Control reactions performed in the absence of dextran and analyzed by gel filtration indicated that the CDAP by itself did not aggregate or polymerize the BSA (protein). A CDAP-treated sample (0.5 ml water+25 µl CDAP @100 mg/ml in acetonitrile+50 µl 0.2M TEA+0.5 ml BSA @10 mg/ml in 0.5M HEPES, pH 8.0) and a control sample (0.575 ml water+0.5 ml BSA (monomeric) @10 mg/ml in 0.5M HEPES, pH 8.0) were prepared. The samples were allowed to react overnight and were quenched with 100 µl of 0.5M ethanolamine in HEPES. After quenching for one hour, the samples were run on a S400 1 cm×50 cm column in saline and azide at 0.75 ml/minute. The OD280 over the column was summed and divided into the sum of the OD280 over the tubes preceding the BSA peak. The CDAP-treated sample showed 0.6% polymeric BSA, and the control sample showed 0.7% polymeric BSA. Thus, the high molecular weight protein is not due to self-polymerization or aggregation.

Moreover, under normal conditions, CDAP does not crosslink the polysaccharide. This was confirmed by the following HPLC experiment where 70 kDa of dextran was activated and then reacted with ethanolamine and run on a gel filtration column. Specifically, 2.5 mg T70 dextran (10 mg/ml) was combined with 20 µl of CDAP (100 mg/ml). At thirty seconds, 20 or 60 µl of 0.2M TEA was added, and at two minutes 100 µl of 0.5M ethanolamine in 0.75M HEPES, pH 7.6, was added. After one hour, samples were run on a G4000 PWXL (Tosohaas) or an SEC3000 (Beckman) in 0.2M NaCl and detected by refractive index (void volume for each column was about 5 minutes, eluting salt at about 10 minutes). No evidence of a shift to higher molecular weight was observed.

As the following comparative experiment shows, extreme conditions should be avoided to prevent the CDAP from crosslinking the polysaccharide. One ml of T2000 dextran (100 mg/ml water) was combined with 176 µl of CDAP (100 mg/ml). After thirty seconds, 176 µl of 0.2M TEA was added, which yielded a gel in less than two minutes.

Figure 13:
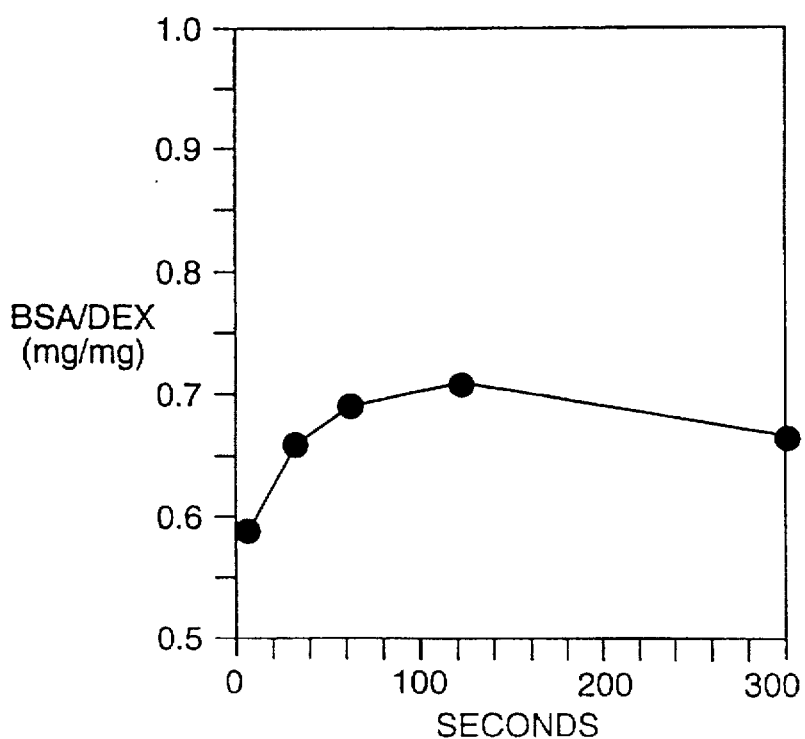
FIG. 13 is a plot of the BSA/dextran ratio versus the time of addition of protein to CDAP-activated dextran.

To determine the optimum activation time and to examine stability of the CDAP-activated polysaccharide, protein (BSA) was added 5–300 seconds after the addition of the CDAP and TEA, and the BSA:dextran ratio of the product was determined. The results shown in FIG. 13 suggest that the optimal activation time is about 2 minutes and that the activated polysaccharide is stable over this time period. If the protein is added at one hour, the reaction yield declines by about one third.

Figure 14:
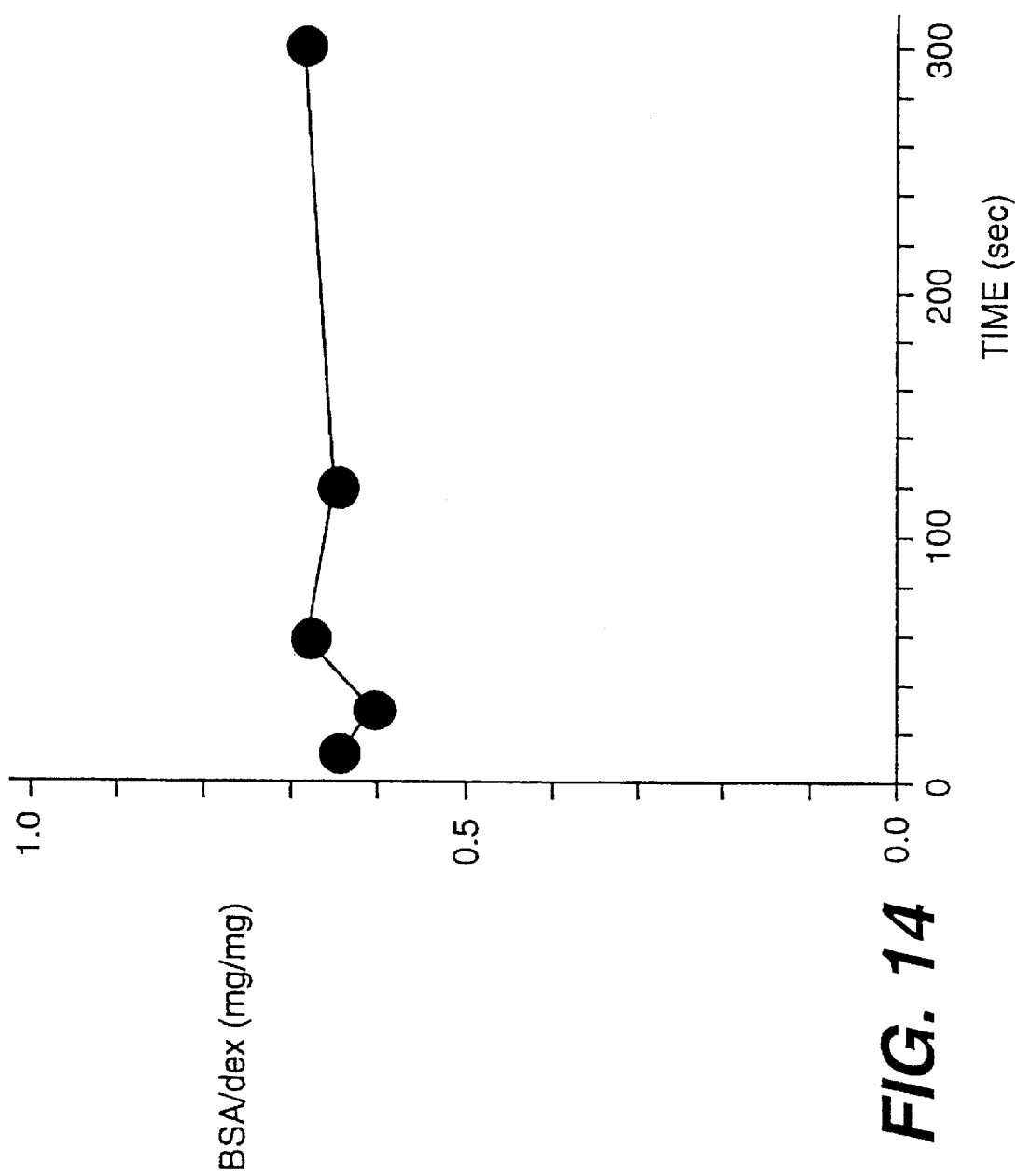
FIG. 14 shows the stability of CDAP in water.

Aqueous mixtures of CDAP and polysaccharides were found to be stable, as reflected in FIG. 14. Sixty µl of CDAP (100 mg/ml) was added to 1 ml water, and 100-µl aliquots of this CDAP solution were combined with 100 µl of polysaccharide (dextran, 20 mg/ml) at various times over a period of 10–300 seconds as shown in FIG. 14, followed 30 seconds later by combination with 15 µl of a TEA solution (0.2M). Two minutes after being combined with the TEA, 100 µl of BSA (30 mg/ml) was added. The reaction was quenched at 48 hours.

No significant differences were found in the final protein-to-polysaccharide ratios over the entire range of addition times. The results shown in FIG. 14 are consistent with the stability of CDAP in acidic solutions and the observation that solutions of CDAP in water become acidic. Thus, water can be substituted for the organic solvent if the reagent solution is to be used the same day. Alternatively, CDAP can be added as a solid to the solution of polysaccharide. In working with small amounts of CDAP, it has been found more convenient to work with solutions than to work with the solid reagent. Furthermore, whereas the rapid addition of an acetonitrile solution of CDAP will sometimes precipitate the polysaccharide, precipitation can be avoided if an aqueous solution of CDAP is used. Aqueous stock solutions of CDAP can be prepared at concentrations up to 75 mg/ml.

Figure 15:
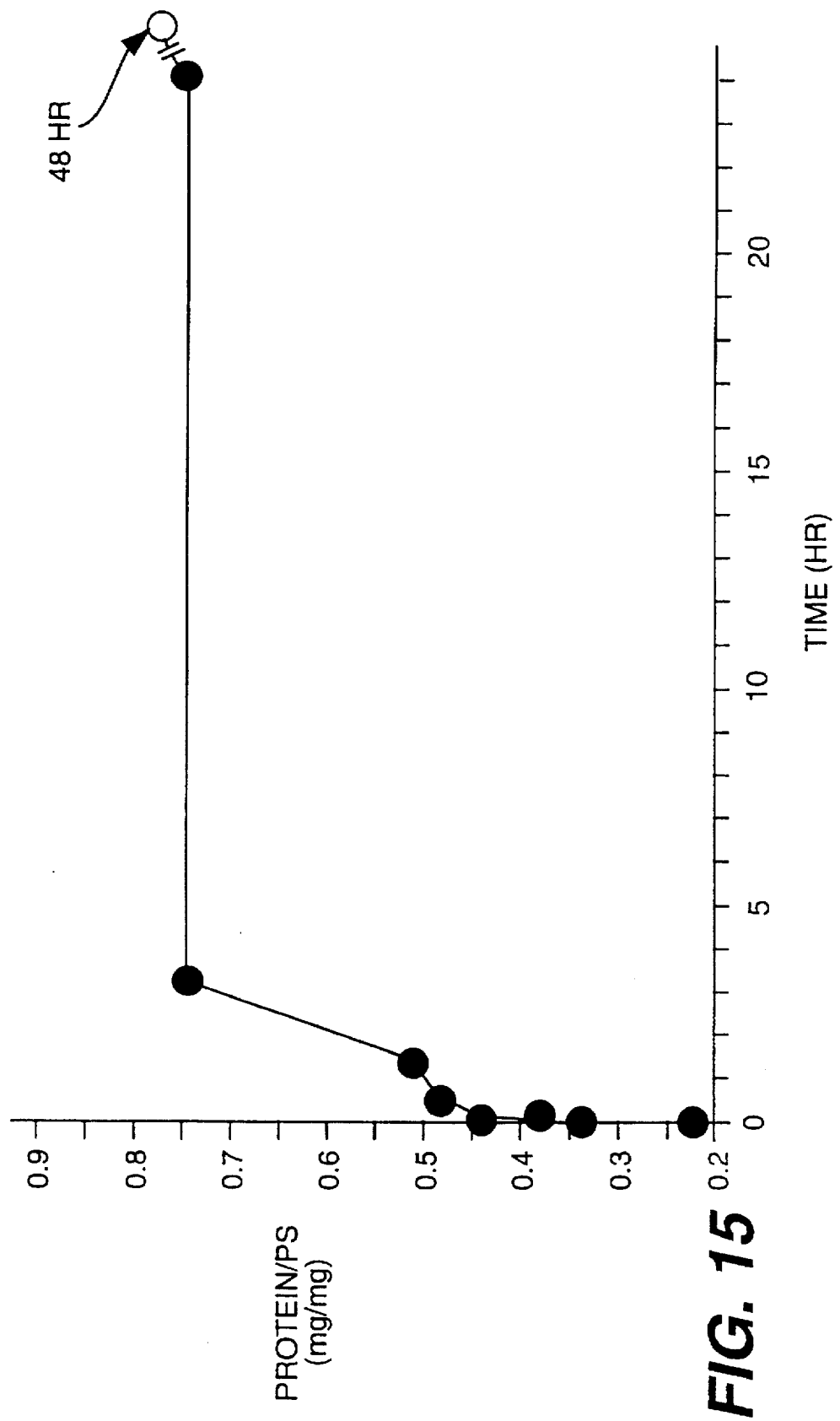
FIG. 15 illustrates the kinetics of protein coupling to CDAP-activated polysaccharide.

FIG. 15 shows that protein conjugation to the polysaccharide was relatively rapid, and within three hours 80% of the maximum conjugation had been attained. Even more rapid coupling could be achieved by increasing the protein concentration, the polysaccharide concentration, and/or the CDAP concentration.

Figure 16:
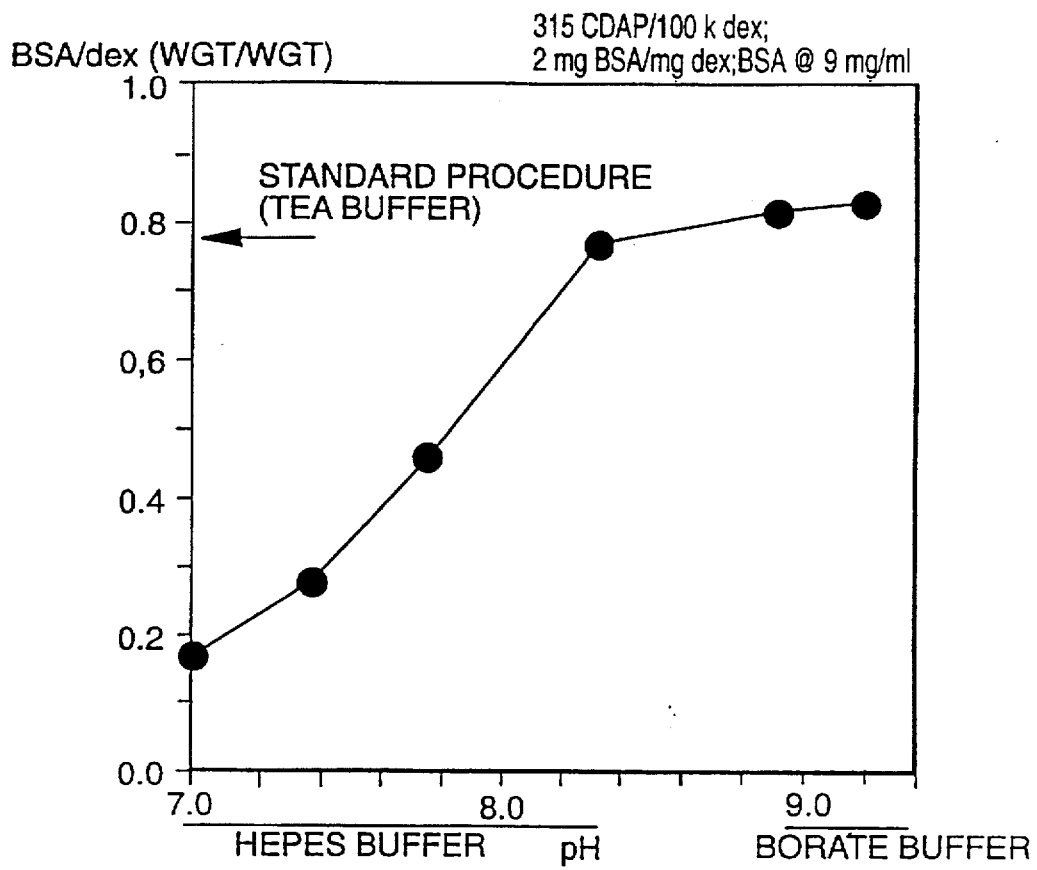
FIG. 16 shows the effect of pH on CDAP activation.

As indicated in FIG. 16, the pH of the reaction solution during the polysaccharide activation is another important parameter in polysaccharide activation with CDAP. As the pH during the activation step was increased from 7.0 to 8.3, there was an increase in polysaccharide activation as reflected by a marked increase in coupling efficiency. The BSA:dextran ratio of the conjugate increased 4-fold as the pH increased from 7.0 to 8.3. At a pH higher than 8.3, there was little or no increase in the ratio. The pH dependence of CDAP activation explains the low level of derivatization that was previously observed in the absence of TEA, since the pH of a CDAP solution in water is initially near neutral and becomes more acidic.

As was noted earlier with respect to the derivatization of polysaccharides with amines, a tertiary amine buffer is not necessary during activation of the polysaccharide for the direct conjugation of proteins. Thus, direct conjugation of protein to polysaccharides may be done, e.g., using a pH stat or automatic titrator to raise the pH during the activation step. This could be advantageous in preparing vaccine conjugates.

Figure 17:
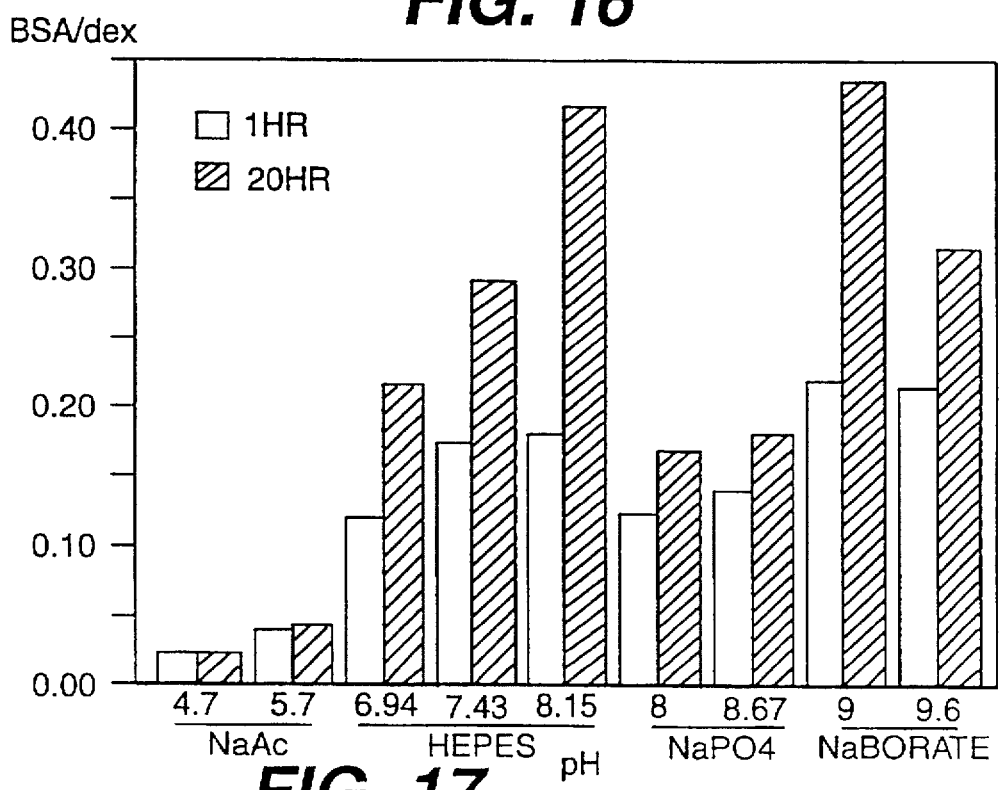
FIG. 17 is a bar graph showing the effect of pH and various buffers on the coupling of BSA to CDAP-activated dextran.

FIG. 17 illustrates that the pH of the reaction solution during the coupling of the protein to the activated polysaccharide is an important parameter in the direct conjugation of protein with CDAP. In the experiment for which results are reported in FIG. 17, several buffers were tested over a wide range of pH values and at a low protein-to-polysaccharide ratio. The protocol was as follows.

To four ml of T2000 dextran (10 mg/ml in water) was added 133 µl of a CDAP solution (100 mg/ml in acetonitrile, freshly prepared) (0.33 mg CDAP/mg dex). After 30 seconds, 266 µl of TEA (from a 0.2M stock) was added, and the pH reached a maximum of 9.6. After 2½ minutes, the pH was adjusted to 5.0 using 60 µl of 1M NaAc (sodium acetate). Four hundred µl of activated dextran was transferred to tubes containing 200 µl of BSA (15 mg/ml) (0.8 mg BSA/mg dex) and 100 µl of a buffer (1M NaAc, pH 4.7, 5.7; 0.5M HEPES, pH 6.94, 7.43, 8.15; 0.1M $NaPO_4$, pH 8.0, 8.67; 50 mM sodium borate, pH 9.0, 9.6) (not controlled for ionic strength). One hour after transfer, 350 µl of the solution of a tube were combined with 100 µl of freshly prepared 0.5M ethanolamine in 0.75M HEPES (pH 7.5). Twenty hours later, 100 µl of ethanolamine were added to the remaining solution. The reaction was quenched for at least two hours and the product run on S300HR or S400HR columns equilibrated with saline plus azide. The peak void volume tube was assayed for BSA using the BioRad assay and for polysaccharide using the resorcinol assay.

As shown in FIG. 17, most of the protein was coupled to the polysaccharide at a pH as low as 7.4, a substantial amount was coupled at a pH as low as 6.9, and a small but significant amount was coupled even at a pH as low as 5.7. For the conditions of this experiment, a pH of about 8 appeared to be optimal. Although the results show that the pH of the coupling step is important, they show that coupling can be done over a wide pH range. Since the coupling reaction is so inefficient at a pH of 5, however, quenching should be done at about a pH of 7 to 8.

Increased amounts of coupling can be obtained even at low pH by increasing the protein-to-polysaccharide ratio, the polysaccharide concentration, and/or the amount of CDAP used. For example, by using more reagent or more protein, higher yields can be obtained even at a pH of 7. Thus, direct protein coupling can be achieved at a near-neutral pH using CDAP to activate the polysaccharide.

FIG. 17 indicates that phosphate is also inhibitory to the coupling reaction, which may be due to ionic interactions or to the slight nucleophilic character of the phosphate. Increasing the amount of CDAP and the pH during the coupling, however, will increase the conjugation ratio/yield. If phosphate is present during the CDAP activation, addition of the diamine is inhibited.

Phosphates of PRP and Pn6 may cause inhibition, as shown by the following experiment. Twenty µl of CDAP (100 mg/ml in acetonitrile) was added to a vortexed solution of 2 mg Pn6 (Pneumococcal type 6, a polyribitol phosphate polysaccharide) (10 mg/ml in water). Thirty seconds later, buffer (100 µl of 0.1M sodium borate or 40 µl of 0.2M TEA) was added. At two minutes, 100 µl of BSA (20 mg/ml) in 0.5M HEPES, pH 8, was added. After incubating overnight at 4° C., the reaction was quenched with 100 µl of 0.5M ethanolamine in 0.75M HEPES, pH 7.5, followed by gel filtration on an S400HR column (Pharmacia) equilibrated with saline and 0.02% azide. The peak void volume tube was assayed for protein and polysaccharide. For comparative purposes, in trial 4 dextran was derivatized in the same manner. The results are reported in Table 12 below.

TABLE 12

| Trial | Ps | Buffer | BSA/Ps (mg/mg) |
|---|---|---|---|
| 1 | Pn6 | 0.2 M TEA | 0.06 |
| 2 | Pn6 | 0.1 M sodium borate (pH 8.8) | 0.16 |
| 3 | Pn6 | 0.1 M sodium borate (pH 10) | 0.31 |
| 4 | dex | 0.1 M sodium borate (pH 8.8) | 0.77 |

For Pn6 with the TEA buffer (trial 1), the yield was very low. As the pH was increased with sodium borate (trials 2 and 3), the yield increased. The same conditions give much higher yields for dextran (see, e.g., trial 4). Thus, phosphate-based polysaccharides such as Pn6 require adjustment in the pH and/or CDAP ratio to prepare conjugates in good yields.

The next experiment shows that the isourea bond formed by CDAP activation is stable and robust. In this experiment, ε-TNP-lysine was coupled to dextran via CDAP. Samples 1–5 were made up as follows:

1: 400 µl TNP/CDAP/dex+100 µl saline (control)
2: 400 µl TNP/CDAP/dex+100 µl 2M NaCl
3: 400 µl TNP/CDAP/dex+100 µl 9M GuHCl
4: 400 µl TNP/CDAP/dex+100 µl saline (reacted in incubator @37° C.)
5: 400 µl TNP/CDAP/dex+100 µl saline (control) The samples were allowed to react overnight in the dark, except example 4, which was reacted as indicated. The samples were then desalted on a P6 cartridge in 10 mM sodium borate at 1.0 ml/minute. The fractions were read at OD366 and the peak tube of the void fractions was assayed. The results are provided in Table 13 below.

TABLE 13

| Sample | TNP (µM) | Dex (µM) | TNP/100 kDa dex |
|---|---|---|---|
| 1 | 96 | 9.7 | 10 |
| 2 | 134 | 12 | 11 |
| 3 | 127 | 11 | 12 |
| 4 | 137 | 13 | 11 |
| 5 | 107 | 10 | 11 |

For each sample the TNP:dextran ratio was unchanged, indicating that the isourea bond was stable to the test conditions.

Biological Activity of Conjugates

To determine whether CDAP activation of the polysaccharide had any detrimental effect on its ability to induce antibody responses, its biological activity in vitro was tested. BSA was either directly conjugated to CDAP-activated Pneumococcal polysaccharide type 14 or coupled to Pneumococcal polysaccharide type 14 derivatized with hexane diamine followed by iodoacetylation and reaction with thiolated protein (Lees et al.). Each conjugate had a ratio of mg BSA/mg Pn14. Inbred DBA/2 mice were immunized subcutaneously with 50 µg of BSA, either free or as a polysaccharide conjugate, in the absence of adjuvants. Sera were collected 14 and 28 days later, and anti-BSA and anti-Pn14 antibody titers determined by ELISA.

Neither unconjugated BSA nor unconjugated Pn14 stimulated a detectable primary response. In contrast, the BSA-Pn14 conjugates stimulated significant antibody responses to both the protein and polysaccharide components, regardless of whether the protein was coupled by indirect conjugation using a spacer or by direct conjugation. Mice immunized with BSA-dextran prepared using a spacer or direct coupling to CDAP-activated dextran gave titers comparable to those obtained when conjugates were prepared using other chemical methods. Moreover, TT-PRP conjugates prepared using CDAP activation have shown in rats immunized with the conjugates anti-PRP responses comparable to those shown in rats immunized with TT-PRP conjugates prepared using CNBr activation. Furthermore, tetanus conjugated directly to CDAP-activated Pn14 had high anti-tetanus and anti-Pn14 antibody responses; opsonic assays indicated that these antibodies were protective.

Summary

The method of the invention utilizing CDAP represents a reproducible approach that can be used to activate various clinically relevant polysaccharides, some of which are sensitive to a high pH. Activation is rapid, so the time is spent at a high pH is minimized. The method produces highly immunogenic protein-polysaccharide conjugates, which can stimulate in mice humoral antibody to both the protein and polysaccharide components even in the absence of adjuvant.

The variables which have been found to profoundly influence the extent of polysaccharide activation are the concentrations of CDAP and polysaccharide, and the pH. A preferred pH for conjugating is about 7 to about 9, more preferably about 7.4 to about 8.0, which is a range at which most polysaccharides are stable. Other pH ranges, e.g., a range of from about 7 to about 10, may be more suitable for other polysaccharides.

By manipulating the polysaccharide and/or CDAP concentration, the efficiency of derivatization can be increased to 50%, as compared to the 1–2% found with CNBr. Furthermore, a product with greater than 50 $NH_2$ groups per 100 kDa of polysaccharide can be achieved under the preferred conditions. The method of the invention does not depend on the presence of tertiary amines, as has been described by previous investigators experimenting with CDAP. The activation of the polysaccharide is rapid. Similarly, protein conjugation to activated polysaccharide is rapid.

The invention offers the advantages of reproducibility, rapid reactivity, and perhaps most notably, the ability to easily manipulate protein:polysaccharide ratios. For example, conjugates with various protein-to-polysaccharide ratios can be achieved by altering the concentration of CDAP and/or the polysaccharide concentration and/or the protein concentration. This may provide an approach to studying not only the role of protein:polysaccharide ratio in influencing the magnitude of the antibody response to the conjugate, but also the role of the three-dimensional structure at a given protein:polysaccharide ratio.

The immunogenicity of the protein-polysaccharide conjugates prepared using CDAP is significantly greater than the response demonstrated by either of the unconjugated components. Furthermore, the antibody that is produced is reactive with the unconjugated protein, and the response can be boosted using the unconjugated protein as well as the conjugated protein. This suggests that any chemical alteration of the protein during conjugation has no detrimental effect on its ability to stimulate antibodies with reactivity to the native protein, nor on its ability to stimulate B cells with reactivity to the unconjugated protein.

Additionally, CDAP-activated polysaccharides can be used in preparation for conjugation of anti-Ig antibodies. Anti-Ig-dextran conjugates induce about 100- to 1000-fold greater activation of B cells as compared to unconjugated Ig. Anti-Ig-dextran conjugates prepared using direct conjugation to CDAP-activated dextran are as effective B-cell stimulatory reagents as the conjugates prepared using other heteroligation coupling to AECM dextran.

CDAP is useful for preparing a variety of immunological reagents, such as biotinylated polysaccharides for ELISA and ELISA spot antigens and TNP-polysaccharides (e.g., TNP-dex, TNP Ficoll) for model Ti-2 antigens.

Thus, the inventive method, which employs CDAP to produce immunogenic constructs such as polysaccharide-based conjugates, offers many advantages to the currently available technology for preparing immunogenic constructs. It will be apparent to those skilled in the art that various modifications in the methods and embodiments of the present invention can be made without departing from the scope or spirit of the invention. Thus, the invention should not be construed to be limited by the description and drawings, but by the appended claims.

2. A method according to claim 1, wherein said organic cyanylating reagent is 1-cyano-4-(dimethylamino)-pyridinium tetrafluoroborate.

3. A method according to claim 2, wherein said polysaccharide and said protein are soluble in water.

4. A method according to claim 3, wherein said activating is carried out at a pH of from 8 to 10, and said coupling is carried out at a pH of from 7 to 9.

5. A method according to claim 2, wherein said activating is carried out in the presence of triethyl amine.

6. A method according to claim 1, wherein said coupling is done indirectly by covalently joining the polysaccharide to a bifunctional or heterofunctional spacer reagent, and covalently joining the protein to the spacer reagent.

7. A method according to claim 6, wherein said spacer reagent is selected from the group consisting of ethylene diamine, 1,6-hexane diamine, adipic dihydrazide, cystamine, glycine, and lysine.

8. A method according to claim 1, wherein the polysaccharide is selected from the group consisting of dextran, Pneumococcal polysaccharide, Haemophilus influenzae polysaccharide, Group A streptococcus polysaccharide, Group B streptococcus polysaccharide, and N. meningitidis polysaccharide.

9. A method according to claim 1, wherein the polysaccharide is a water-soluble viral or bacterial polysaccharide.

10. A method according to claim 1, wherein the protein is a water-soluble protein.

11. A method according to claim 1, wherein the protein is selected from the group consisting of bovine serum albumin, pertussis toxoid, tetanus toxoid, malaria-derived peptide, an antibody, a toxoid, and a lipoprotein.

What is claimed is:

1. In a method for preparing a vaccine comprising an immunogenic construct and a pharmaceutically acceptable carrier, the improvement comprising producing the immunogenic construct by a process comprising:

(a) activating a viral, fungal or bacterial polysaccharide with an organic cyanylating reagent selected from the group consisting of 1-cyano-4-(dimethylamino)-pyridinium tetrafluoroborate, N-cyanotriethyl-ammonium tetrafluoroborate, and p-nitrophenylcyanate, to form an activated carbohydrate; and (b) coupling said activated carbohydrate directly or indirectly to a protein to form the immunogenic construct capable of stimulating an immune response.

12. A method according to claim 1, wherein the immunogenic construct is a conjugate selected from the group consisting of PT-Pn, PT-PRP, TT-Pn, antibody-dextran, and peptide-TT-Pn.

13. A method for producing an immune response in a patient comprising:

(a) preparing a vaccine comprising an immunogenic construct capable of stimulating an immune response and a pharmaceutically acceptable carrier, wherein the immunogenic construct is produced by; (i) activating a viral, fungal or bacterial polysaccharide with an organic cyanylating reagent selected from the group consisting of 1-cyano-4-(dimethylamino)-pyridinium tetrafluoroborate, N-cyanotriethyl-ammonium tetrafluoroborate, and p-nitrophenylcyanate, to form an activated carbohydrate, and (ii) covalently joining said activated carbohydrate to a protein to form the immunogenic construct; and (b) administering the vaccine to said patient.

14. A method according to claim 13, wherein said organic cyanylating reagent is 1-cyano-4-(dimethylamino)-pyridinium tetrafluoroborate.

15. A method according to claim 14, wherein said activating is carried out in the presence of triethyl amine.

16. A method according to claim 14, wherein the protein is a water-soluble protein.

17. A method according to claim 14, wherein the polysaccharide is selected from the group consisting of dextran, Pneumococcal polysaccharide, *Haemophilus influenzae* polysaccharide, Group A streptococcus polysaccharide, Group B streptococcus polysaccharide, and *N. meningitidis* polysaccharide.

18. A method according to claim 14, wherein the protein is selected from the group consisting of bovine serum albumin, pertussis toxoid, tetanus toxoid, malaria-derived peptide, an antibody, a toxoid, and a lipoprotein.

19. A method according to claim 14, wherein the immunogenic construct is a conjugate selected from the group consisting of PT-Pn, PT-PRP, TT-Pn, antibody-dextran, and peptide-TT-Pn.

* * * * *

UNITED STATES PATENT AND TRADEMARK OFFICE
CERTIFICATE OF CORRECTION

PATENT NO.: 5,693,326

DATED: December 2, 1997

INVENTOR(S): Lees et al.

It is certified that an error appears in the above-identified patent and that said Letters Patent is hereby corrected as shown below:

CLAIM 13, Col. 30, L. 61 change "by;" to --by:--.

Face of the patent, change "The portion of the term of this patent subsequent to Mar. 22, 2012, has been disclaimed" to --The portion of the term of this patent subsequent to the expiration date of U.S. Patent No. 5,651,971 has been disclaimed--.

Signed and Sealed this

Twenty-fourth Day of October, 2000

*Attest:*

Q. TODD DICKINSON

*Attesting Officer*   *Director of Patents and Trademarks*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Cys Asn Ile Gly Lys Pro Asn Val Gln Asp Asp Gln Asn Lys
 1               5                  10
```